(12) United States Patent
Khandhar et al.

(10) Patent No.: US 12,133,894 B2
(45) Date of Patent: *Nov. 5, 2024

(54) COMPOSITIONS AND METHODS FOR DELIVERY OF RNA

(71) Applicant: HDT Bio Corp., Seattle, WA (US)

(72) Inventors: Amit Khandhar, Issaquah, WA (US); Steven Reed, Bellevue, WA (US); Malcolm Duthie, Sammamish, WA (US); Jesse Erasmus, Port Orchard, WA (US); Darrick Carter, Seattle, WA (US); Bryan J. Berube, Issaquah, WA (US)

(73) Assignee: HDT Bio Corp., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/390,700

(22) Filed: Dec. 20, 2023

(65) Prior Publication Data
US 2024/0115728 A1   Apr. 11, 2024

Related U.S. Application Data

(63) Continuation of application No. 18/357,280, filed on Jul. 24, 2023, now Pat. No. 11,896,677, which is a
(Continued)

(51) Int. Cl.
*A61K 47/69* (2017.01)
*A61K 9/107* (2006.01)
(Continued)

(52) U.S. Cl.
CPC ........ *A61K 47/6907* (2017.08); *A61K 9/1075* (2013.01); *A61K 9/127* (2013.01);
(Continued)

(58) Field of Classification Search
CPC ............. A61K 47/6907; A61K 9/1075; A61K 31/711; A61K 47/44; A61K 47/6923
See application file for complete search history.

(56) References Cited

U.S. PATENT DOCUMENTS

| 7,045,335 | B2 | 5/2006 | Smith |
| 7,425,337 | B2 | 9/2008 | Smith |
| | | (Continued) | |

FOREIGN PATENT DOCUMENTS

| WO | 2001021810 A1 | 3/2001 |
| WO | 2002080982 A2 | 10/2002 |
| | (Continued) | |

OTHER PUBLICATIONS

Feloner: Lipofection: A Highly Efficient, Lipid-Mediated DNA-Transfection Procedure, Proc. Natl Acad Sci USA, Biochemistry, vol. 84, pp. 7413-7417. (Year: 1987).*
(Continued)

*Primary Examiner* — Carlos A Azpuru
(74) *Attorney, Agent, or Firm* — Greenberg Traurig, LLP; Lisa L. Scudder

(57) ABSTRACT

The disclosure provides nanoemulsion compositions and methods of making and using thereof to deliver a bioactive agent such as a nucleic acid to a subject. The nanoemulsion composition comprises a hydrophobic core based on inorganic nanoparticles in a lipid nanoparticle that allows imaging as well as delivering nucleic acids. Methods of using these particles for treatment and vaccination are also provided.

22 Claims, 22 Drawing Sheets

Related U.S. Application Data continuation of application No. 17/839,574, filed on Jun. 14, 2022, now Pat. No. 11,752,218, which is a continuation of application No. 17/702,730, filed on Mar. 23, 2022, now Pat. No. 11,433,142, which is a continuation of application No. 17/523,457, filed on Nov. 10, 2021, now Pat. No. 11,318,213, which is a continuation of application No. PCT/US2021/019103, filed on Feb. 22, 2021.

(60) Provisional application No. 62/993,307, filed on Mar. 23, 2020, provisional application No. 63/054,754, filed on Jul. 21, 2020.

(51) Int. Cl.
| | |
|---|---|
| *A61K 9/127* | (2006.01) |
| *A61K 9/51* | (2006.01) |
| *A61K 31/7105* | (2006.01) |
| *A61K 31/711* | (2006.01) |
| *A61K 31/713* | (2006.01) |
| *A61K 39/215* | (2006.01) |
| *A61K 39/39* | (2006.01) |
| *A61K 47/02* | (2006.01) |
| *A61K 47/44* | (2017.01) |
| *A61K 49/18* | (2006.01) |
| *A61P 31/14* | (2006.01) |
| *C07K 14/165* | (2006.01) |
| *C12N 15/86* | (2006.01) |
| *C12N 15/88* | (2006.01) |
| *A61K 39/00* | (2006.01) |
| *A61K 47/10* | (2017.01) |
| *A61K 47/26* | (2006.01) |
| *A61K 47/54* | (2017.01) |
| *B82Y 5/00* | (2011.01) |
| *B82Y 25/00* | (2011.01) |
| *B82Y 30/00* | (2011.01) |
| *B82Y 40/00* | (2011.01) |

(52) U.S. Cl.
CPC .......... *A61K 9/5115* (2013.01); *A61K 9/5123* (2013.01); *A61K 31/7105* (2013.01); *A61K 31/711* (2013.01); *A61K 31/713* (2013.01); *A61K 39/215* (2013.01); *A61K 39/39* (2013.01); *A61K 47/02* (2013.01); *A61K 47/44* (2013.01); *A61K 47/6911* (2017.08); *A61K 47/6923* (2017.08); *A61K 49/183* (2013.01); *A61K 49/1833* (2013.01); *A61P 31/14* (2018.01); *C07K 14/165* (2013.01); *C12N 15/86* (2013.01); *C12N 15/88* (2013.01); *A61K 2039/55555* (2013.01); *A61K 47/10* (2013.01); *A61K 47/26* (2013.01); *A61K 47/547* (2017.08); *B82Y 5/00* (2013.01); *B82Y 25/00* (2013.01); *B82Y 30/00* (2013.01); *B82Y 40/00* (2013.01); *C12N 2770/36143* (2013.01)

(56) References Cited

U.S. PATENT DOCUMENTS

| | | | |
|---|---|---|---|
| 8,709,441 B2 | 4/2014 | Rayner | |
| 8,734,832 B2 | 5/2014 | O'Hagan et al. | |
| 8,853,179 B2 | 10/2014 | Mauro | |
| 9,295,646 B2 | 3/2016 | Brito et al. | |
| 9,555,136 B2 | 1/2017 | Khandhar et al. | |
| 9,655,845 B2 | 5/2017 | Brito | |
| 10,238,733 B2 | 3/2019 | Brito | |
| 10,307,374 B2 | 6/2019 | Brito | |
| 11,026,890 B2 | 6/2021 | Brito | |
| 11,083,786 B2 | 8/2021 | Kamrud | |
| 11,135,287 B2 | 10/2021 | Brito | |
| 11,141,377 B2 | 10/2021 | Fox | |
| 11,318,213 B2 * | 5/2022 | Khandhar | A61K 47/02 |
| 11,364,310 B2 | 6/2022 | Kamrud | |
| 11,752,218 B2 * | 9/2023 | Khandhar | A61K 47/6923 514/44 R |
| 2006/0128011 A1 | 6/2006 | Zhu | |
| 2009/0252721 A1 | 10/2009 | Buschmann | |
| 2012/0156251 A1 | 6/2012 | Brito | |
| 2013/0195751 A1 | 8/2013 | Hahn | |
| 2016/0000886 A1 | 1/2016 | Parker | |
| 2016/0201067 A1 | 7/2016 | Ataullakhanov | |
| 2017/0189368 A1 | 7/2017 | Troiano | |
| 2018/0008694 A1 | 1/2018 | Ciaramella | |
| 2018/0104325 A1 | 4/2018 | Gale, Jr. | |
| 2018/0147298 A1 | 5/2018 | Besin | |
| 2018/0153848 A1 | 6/2018 | Chen | |
| 2018/0207295 A1 | 7/2018 | Fotin-Mleczek | |
| 2019/0015501 A1 | 1/2019 | Ciaramella | |
| 2019/0274968 A1 | 9/2019 | Weissman | |
| 2020/0006973 A1 | 1/2020 | Petersen | |
| 2020/0069599 A1 | 3/2020 | Smith | |
| 2020/0123573 A1 | 4/2020 | Kamrud | |
| 2020/0157571 A1 | 5/2020 | Nakanishi | |
| 2020/0224174 A1 | 7/2020 | Irvine | |
| 2020/0230056 A1 | 7/2020 | Fox | |
| 2020/0297834 A1 | 9/2020 | Kehn-Hall | |
| 2020/0368344 A1 | 11/2020 | Ciaramella | |
| 2020/0370052 A1 | 11/2020 | Wilson | |
| 2021/0128583 A1 | 5/2021 | Zhang | |
| 2021/0283242 A1 | 9/2021 | Hutchins | |
| 2021/0290752 A1 | 9/2021 | Sullivan | |
| 2021/0290756 A1 | 9/2021 | Sullivan | |
| 2021/0330781 A1 | 10/2021 | Kamrud | |

FOREIGN PATENT DOCUMENTS

| | | |
|---|---|---|
| WO | 2005107760 A1 | 11/2005 |
| WO | 2007024826 A2 | 3/2007 |
| WO | 2008124647 A2 | 10/2008 |
| WO | 2008153541 A1 | 12/2008 |
| WO | WO2009049083 | 4/2009 |
| WO | 2010141861 A1 | 12/2010 |
| WO | WO 2011/156761 | 12/2011 |
| WO | 2014042780 A1 | 3/2014 |
| WO | 2015103167 A2 | 7/2015 |
| WO | 2017200852 A1 | 11/2017 |
| WO | 2017200957 A1 | 11/2017 |
| WO | 2017205225 A2 | 11/2017 |
| WO | 2017210364 A1 | 12/2017 |
| WO | 2017218704 A1 | 12/2017 |
| WO | WO2018022957 | 2/2018 |
| WO | 2018/044028 | 3/2018 |
| WO | 2018053294 A1 | 3/2018 |
| WO | WO 2018/147710 | 8/2018 |
| WO | 2018232257 | 12/2018 |
| WO | WO20182322257 | 12/2018 |
| WO | WO 2019/152884 | 8/2019 |
| WO | 2020132279 A1 | 6/2020 |
| WO | 2020/243115 | 12/2020 |
| WO | 2020254804 A1 | 12/2020 |
| WO | 2021021605 A1 | 2/2021 |
| WO | 2021076630 A1 | 4/2021 |
| WO | WO 2021/067480 | 4/2021 |
| WO | WO 2021/072112 | 4/2021 |
| WO | WO 2021/163536 | 8/2021 |
| WO | 2021178886 A1 | 9/2021 |
| WO | 2021183564 A1 | 9/2021 |
| WO | 2021194672 A1 | 9/2021 |
| WO | WO 2021/194672 | 9/2021 |
| WO | 2021210686 A1 | 10/2021 |
| WO | WO 2022/051022 | 3/2022 |
| WO | 2022136952 A1 | 6/2022 |
| WO | 2023286076 A1 | 1/2023 |
| WO | 2023/049636 A2 * | 3/2023 |
| WO | 2023026301 A1 | 3/2023 |
| WO | 2023049363 A1 | 3/2023 |

(56) References Cited

FOREIGN PATENT DOCUMENTS

| WO | 2023049636 A1 | 3/2023 |
|---|---|---|
| WO | 2023056202 A2 | 4/2023 |

OTHER PUBLICATIONS

Agnihothram, S., et al., "Development of a Broadly Accessible Venezuelan Equine Encephalitis Virus Replicon Particle Vaccine Platform" J Virol. May 14, 2018;92(11):e00027-18. doi: 10.1128/JVI.00027-18.

Anderluzzi, G., et al., "Investigating the Impact of Delivery System Design on the Efficacy of Self-Amplifying RNA Vaccines" Vaccines (Basel). May 8, 2020;8(2):212. doi: 10.3390/vaccines8020212.

Bazhan, S., et al., "Immunogenicity and Protective Efficacy of Influenza A DNA Vaccines Encoding Artificial Antigens Based on Conservative Hemagglutinin Stem Region and M2 Protein in Mice." Vaccines vol. 8,3 448. Aug. 9, 2020, doi:10.3390/vaccines8030448.

Boettler, T., et al., "SARS-CoV-2 vaccination can elicit a CD8 T-cell dominant hepatitis" J Hepatol. Sep. 2022;77(3):653-659. doi: 10.1016/j.jhep.2022.03.040.

Chiu, C.Y.H., et al., "Association of antibodies to Plasmodium falciparum reticulocyte binding protein homolog 5 with protection from clinical malaria" Front Microbiol. Jun. 30, 2014;5:314. doi: 10.3389/fmicb.2014.00314.

Du, L., et al., "The Spike Protein of SARS-CoV—A Target for Vaccine and Therapeutic Development", Nat Rev Microbiol 7, 226-236 (2009). https://doi.org/10.1038/nrmicro2090.

Duerrwald, R., et al., "Influenza A virus (A/swine/Bueren/5439/2006(H3N2)) segment 4 hemagglutinin (HA) gene, complete cds". Genbank entry (online). National Center for Biotechnology Information. URL: Https://www.ncbi.nlm.nih.gov/nucleotide/MK362039.1J. Jan. 31, 2020; pp. 1-2.

Fleeton, M. N., et al., "Self-Replicative RNA Vaccines Elicit Protection Against Influenza A Virus, Respiratory Syncytial Virus, and a Tickborne Encephalitis Virus", The Journal of Infectious Diseases, vol. 183, Issue 9, May 1, 2001, pp. 1395-1398, https://doi.org/10.1086/319857.

Fox, C.B., "Squalene emulsions for parenteral vaccine and drug delivery" Molecules. Sep. 1, 2009;14(9):3286-312. doi: 10.3390/molecules14093286.

Gao, Y., et al, "Structure of the RNA-dependent RNA polymerase from COVID-19 virus" Science. May 15, 2020;368(6492):779-782. doi: 10.1126/science.abb7498.

Gehardt, Alana, et al., "A flexible, thermostable nanostructured lipid carrier platform for RNA vaccine delivery" Mol Ther Methods Clin Dev. Jun. 9, 2022;25:205-214. doi: 10.1016/j.omtm.2022.03.009.

Hatmal, M.M., et al., "Comprehensive Structural and Molecular Comparison of Spike Proteins of SARS-CoV-2, SARS-CoV and MERS-CoV, and Their Interactions with ACE2" Cells Dec. 8, 2020;9(12):2638. doi: 10.3390/cells9122638.

Hawman, D. W. et al., "SARS-CoV2 variant-specific replicating RNA vaccines protect from disease and pathology and reduce viral shedding following challenge with heterologous SARS-CoV2 variants of concern" bioRxiv [Preprint]. Dec. 13, 2021:2021.12.10.472134. doi: 10.1101/2021.12.10.472134 bioRxiv 2021.12.10.472134; doi: https://doi.org/10.1101/2021.12.10.472134.

Heinz, F.X., and Stiasny, K., "Distinguishing features of current COVID-19 vaccines: knowns and unknowns of antigen presentation and modes of action" NPJ Vaccines. Aug. 16, 2021;6(1):104. doi: 10.1038/s41541-021-00369-6.

Huang, H.C., et al., "Formulation of novel lipid-coated magnetic nanoparticles as the probe for in vivo imaging" J Biomed Sci. Sep. 21, 2009;16(1):86. doi: 10.1186/1423-0127-16-86.

Huang, Y., et al., "Structural and functional properties of SARS-CoV-2 spike protein: potential antivirus drug development for COVID-19" Acta Pharmacol Sin 41, 1141-1149 (2020). https://doi.org/10.1038/s41401-020-0485-4.

International Search Report issued Jun. 6, 2022 in PCT/US2022/13513.

International Search Report issued Jun. 8, 2022 in PCT/US2022/013516.

International Search Report issued Jun. 14, 2022 in PCT/US2022/13508.

International Search Report issued in PCT/US2023/060225 dated Jul. 28, 2023.

Kautz, T. F., et al., "Low-fidelity Venezuelan equine encephalitis virus polymerase mutants to improve live-attenuated vaccine safety and efficacy" Virus Evol.:4(1); pp. 1-14, Mar. 6, 2018;. doi: 10.1093/ve/vey004.

Kimuira, T, et al., "A localizing nanocarrier formulation enables multi-target immune responses to multivalent replicating RNA with limited systemic inflammation", Molecular Therapy (2023), doi: https://doi.org/10.1016/j.ymthe.2023.06.017.

Kwon, S.M., et al., "In vivo time-dependent gene expression of cationic lipid-based emulsion as a stable and biocompatible non-viral gene carrier" J Control Release. May 22, 2008;128(1):89-97. doi: 10.1016/j.jconrel.2008.02.004. Epub Feb. 19, 2008. Erratum in: J Control Release. Nov. 16, 2009;140(1):74.

Marcus, M., et al., "Iron oxide nanoparticles for neuronal cell applications: uptake study and magnetic manipulations", J Nanobiotechnology, vol. 14, Issue 37, May 2016, https://doi.org/10.1186/s12951-016-0190-0.

Maruggi, G., et al., "A self-amplifying mRNA SARS-CoV-2 vaccine candidate induces safe and robust protective immunity in preclinical models" Mol Ther. Jan. 3, 2022:S1525-0016(22)00001-6. doi: 10.1016/j.ymthe.2022.01.001.

Min, J. W., et al., "Hemagglutinin (Influenza A virus (A/Aichi/2/1968(H3N2))]". Genbank entry (online). National Center for Biotechnology Information. Retrieved From The Internet. URL: https://www.ncbi.nlm.nih.gov/protein/AAA43239.1]. Jul. 13, 2006; p. 1.

Oscherwitz, J., et al., "A heterologous helper T-cell epitope enhances the immunogenicity of a multiple-antigenic-peptide vaccine targeting the cryptic loop-neutralizing determinant of Bacillus anthracis protective antigen" Infect Immun. Dec. 2009;77(12):5509-18. doi: 10.1128/IAI.00899-09.

Pardi, N., et al., "mRNA vaccines—a new era in vaccinology" Nat Rev Drug Discov. Apr. 2018;17(4):261-279. doi: 10.1038/nrd.2017.243. Epub Jan. 12, 2018. PMID: 29326426.

Roeffen, W., et al., "Transmission-blocking activity of antibodies to Plasmodium falciparum GLURP.10C chimeric protein formulated in different adjuvants" Malar J 14, 443 (2015). https://doi.org/10.1186/s12936-015-0972-0.

Romagnani, S., "h1 and Th2 in human diseases" Clin Immunol Immunopathol. Sep. 1996;80(3 Pt 1):225-35. doi: 10.1006/clin.1996.0118.

Safety And Immunogenicity Of HDT-301 Targeting A SARS-CoV-2 Variant Spike Protein, Sponsor: HDT Bio, posted 11/24/21ClinicalTrials.gov Identifier: NCT05132907 found at https://clinicaltrials.gov/ct2/show/record/NCT05132907?term=hdt+bio&draw=2&rank=1 11 pages.

Schoenmaker, L., et al. "mRNA-lipid nanoparticle COVID-19 vaccines: Structure and stability." International journal of pharmaceutics vol. 601 (2021): 120586. doi:10.1016/j.ijpharm.2021.120586.

Shu, B., et al., "Structural basis of viral RNA-dependent RNA polymerase catalysis and translocation", Proc Natl Acad Sci USA; 113(28):E4005-14, Jun. 23, 2016 doi: 10.1073/pnas.1602591113.

Singh, K., et al., "Malaria vaccine candidate based on Duffy-binding protein elicits strain transcending functional antibodies in a Phase I trial" NPJ Vaccines. Sep. 28, 2018;3:48. doi: 10.1038/s41541-018-0083-3.

Starmans, L.W.E., et al., "Iron oxide nanoparticle-micelles (ION-micelles) for sensitive (molecular) magnetic particle imaging and magnetic resonance imaging" PLoS One. 2013;8(2):e57335. doi: 10.1371/journal.pone.0057335. Epub Feb. 20, 2013.

Stokes, A., et al., "Nonclinical safety assessment of repeated administration and biodistribution of a novel rabies self-amplifying mRNA vaccine in rats" Regul Toxicol Pharmacol. Jun. 2020;113:104648. doi: 10.1016/j.yrtph.2020.104648.

Teixeira, T. et al., "Cationic nanoemulsions as nucleic acids delivery systems" Int J Pharm. Dec. 20, 2017;534(1-2):356-367. doi: 10.1016/j.ijpharm.2017.10.030.

(56) References Cited

OTHER PUBLICATIONS

Tregoning, J. S., et al., "Formulation, inflammation, and RNA sensing impact the immunogenicity of self-amplifying RNA vaccines" Mol Ther Nucleic Acids. Dec. 5, 2022;31:29-42. doi: 10.1016/j.omtn.2022.11.024.

Tregoning, J.S.. "LION: Taming RNA vaccine inflammation" Mol Ther. Aug. 3, 2023:S1525-0016(23)00386-6. doi: 10.1016/j.ymthe.2023.07.006.

Valdivia, L, et al., Solid Lipid Particles for Lung Metastasis Treatment. Pharmaceutics. 2021;13(1):93. Published Jan. 13, 2021. doi:10.3390/pharmaceutics13010093.

Voigt, E.A., et al., "A self-amplifying RNA vaccine against COVID-19 with long-term room-temperature stability" npj Vaccines 7, 136 (2022). https://doi.org/10.1038/s41541-022-00549-y.

Walton, T.E., et al., "Experimental infection of horses with an attenuated Venezuelan equine encephalomyelitis vaccine (strain TC-83)" Infect Immun. May 1972;5(5):750-6. doi: 10.1128/iai.5.5.750-756.1972.

Wu, F., et al., "Severe acute respiratory syndrome coronavirus 2 isolate Wuhan-Hu-1, complete genome" GenBank: MN908947.3, VRL Mar. 18, 2020, available at https://www.ncbi.nlm.nih.gov/nuccore/MN908947.

"Gennova's mRNA vaccine to come in powder form; will stay stable at 2-8° C." Business Standard. Sep. 13, 2021 02:56 IST.

Brinckerhoff, L. H., et al., "Melanoma vaccines" Current Opinion in Oncology: Mar. 2000—vol. 12—Issue 2—p. 163-173.

Brito, L.. A.., et al., A cationic nanoemulsion for the delivery of next-generation RNA vaccines. Mol Ther. 2014;22(12):2118-2129. doi:10.1038/mt.2014.133.

Brocato, R. L., et al., Protective efficacy of a SARS-CoV-2 DNA vaccine in wild-type and immunosuppressed Syrian hamsters. NPJ Vaccines 6, 16 (2021). https://doi.org/10.1038/s41541-020-00279-z.

Brown, C. M., et al. Outbreak of SARS-CoV-2 Infections, Including COVID-19 Vaccine Breakthrough Infections, Associated with Large Public Gatherings—Barnstable County, Massachusetts, Jul. 2021. MMWR Morb Mortal Wkly Rep 2021;70:1059-1062.

Corbett, K. S., et al., "Evaluation of the mRNA-1273 Vaccine against SARS-CoV-2 in Nonhuman Primates" N Engl J Med. Oct. 15, 2020;383(16):1544-1555. doi: 10.1056/NEJMoa2024671.

Corman, V. C., et al., Detection of 2019 novel coronavirus (2019-nCoV) by real-time RT-PCR. Euro Surveill. 2020;25(3), https://doi.org/10.2807/1560-7917.ES.2020.25.3.2000045.

CustomBiotech Online Development Exchange (CODE), Beyond COVID: The Future of mRNA technology, Webinar held Thursday, Nov. 11, 2021, https://dianews.roche.com/CustomBiotech-Webinar-2021.html.

Edara, V., et al., Infection and Vaccine-Induced Neutralizing-Antibody Responses to the SARS-CoV-2 B.1.617 Variants. N Engl J Med. Aug. 12, 2021;385(7):664-666. doi: 10.1056/NEJMc2107799. Epub Jul. 7, 2021. PMID: 34233096; PMCID: PMC8279090.

Erasmus, J. H., A Nanostructured Lipid Carrier for Delivery of Replicating Viral RNA Provides Single, Low-Dose Protection against Zika, Molecular Therapy, vol. 26, No. 10. pp. 2507-2522.

Erasmus, J. H., et al., "An Alphavirus-derived replicon RNA vaccine induces SARS-CoV-2 neutralizing antibody and T cell responses in mice and nonhuman primates" Science Translational Medicine, Aug. 5, 2020, vol. 12, Issue 555.

Erasmus, J.H. et al., "Single-dose Replicating RNA Vaccine Induces Neutralizing Antibodies Against SARS-CoV-2 in Nonhuman Primates", bioRxiv, 28 pages.

Erasmus, J.H., "An Alphavirus-derived replicon RNA vaccine induces SARS-CoV-2 Neutralizing Antibody and T-cell Responses in Mice and Nonhuman Primates", Science Translational Medicine, vol. 12, No. 555.

Erasmus, J.H., et al., Intramuscular Delivery of Replicon RNA Encoding ZIKV-117 Human Monoclonal Antibody Protects against Zika Virus Infection. Mol Ther—Methods Clin Dev. 2020;18:402-414. PMID: 32695842.

File No. BIO/CT/20/000182, CT No. CT-02/2021 Government of India Directorate General of Health Services Central Drugs Standard Control Organization (Biological Division), Form CT-06 Permission to Conduct Clinical Trial of New Drug or Investigational New Drug, Jan. 25, 2021, 3 pages.

File No. BIO/CT/21/000105, CT No. CT-28/2021 Government of India Directorate General of Health Services Central Drugs Standard Control Organization (Biological Division), Form CT-06 Permission to Conduct Clinical Trial of New Drug or Investigational New Drug, Aug. 22, 2021, 3 pages.

Fischer, Robert J., et al. "ChAdOx1 nCoV-19 (AZD1222) protects Syrian hamsters against SARS-CoV-2 B.1.351 and B.1.1.7." bioRxiv : the preprint server for biology 2021.03.11.435000. Jun. 30, 2021, doi:10.1101/2021.03.11.435000. Preprint.

Geall, Andrew J., et al. "Nonviral delivery of self-amplifying RNA vaccines." PNAS. vol. 109. No. 36, pp. 14604-14609 (2012).

Gilchuk, P., et al., "Integrated pipeline for the accelerated discovery of antiviral antibody therapeutics" Nat Biomed Eng. 2020;4(11):1030-1043. PMID: 32747832.

Hörner, C., et al., A highly immunogenic and effective measles virus-based Th1-biased COVID-19 vaccine, Proceedings of the National Academy of Sciences Dec. 2020, 117 (51) 32657-32666; DOI: 10.1073/pnas.2014468117.

Hou, X., et al., Lipid nanoparticles for mRNA delivery. Nat Rev Mater (2021). https://doi.org/10.1038/s41578-021-00358-0.

International Search Report and Written Opinion for PCT/US2021/019103 issued Sep. 30, 2021.

Jain, T.K., et al., Iron Oxide Nanoparticles for Sustained Delivery of Anticancer Agents, Molecular Pharmaceutics, American Chemical Society, 2 (3), 194-205, 2005.

Kalnin, K.V., et al., Immunogenicity and efficacy of mRNA COVID-19 vaccine MRT5500 in preclinical animal models. npj Vaccines 6, 61 (2021). https://doi.org/10.1038/s41541-021-00324-5.

Kurup, D. et al., Inactivated rabies virus vectored SARS-CoV-2 vaccine prevents disease in a Syrian hamster model, PLOS Pathogens 17(3): e1009383. https://doi.org/10.1371/journal.ppat.1009383.

Li, Q. et al., "A Review of the Structure, Preparation, and Application of NLCs, PNPs and PLNs", Nanomaterials, vol. 7, No. 6, p. 1-25.

Limbach, P A et al. "Summary: the modified nucleosides of RNA." Nucleic acids research vol. 22,12 (1994): 2183-96. doi:10.1093/nar/22.12.2183.

Lopez Bernal, J, et al., Effectiveness of Covid-19 Vaccines against the B.1.617.2 (Delta) Variant. N Engl J Med. Aug. 12, 2021;385(7):585-594. doi: 10.1056/NEJMoa2108891. Epub Jul. 21, 2021. PMID: 34289274; PMCID: PMC8314739.

Machado, B.A.S., et al., The Importance of RNA-Based Vaccines in the Fight against COVID-19: An Overview. Vaccines (Basel). Nov. 17, 2021;9(11):1345. doi: 10.3390/vaccines9111345. PMID: 34835276; PMCID: PMC8623509.

Mckay, P. F., et al., Self-amplifying RNA SARS-CoV-2 lipid nanoparticle vaccine candidate induces high neutralizing antibody titers in mice. Nat Commun. Jul. 9, 2020;11(1):3523. doi: 10.1038/s41467-020-17409-9. PMID: 32647131; PMCID: PMC7347890.

Mercado, N.B., et al., "Single-shot Ad26 vaccine protects against SARS-CoV-2 in rhesus macaques" Nature. Oct. 2020;586(7830):583-588. doi: 10.1038/s41586-020-2607-z. Epub Jul. 30, 2020. Erratum in: Nature. Feb. 2021;590(7844):E25. PMID: 32731257; PMCID: PMC7581548.

Meyer, B., et al., Characterising proteolysis during SARS-CoV-2 infection identifies viral cleavage sites and cellular targets with therapeutic potential. Nat Commun. Sep. 21, 2021;12(1):5553. doi: 10.1038/s41467-021-25796-w. PMID: 34548480; PMCID: PMC8455558.

Mohandas, S., et al., Immunogenicity and protective efficacy of BBV152, whole virion inactivated Sars-CoV-2 vaccine candidates in the Syrian hamster model. iScience. Feb. 19, 2021;24(2):102054. doi: 10.1016/j.isci.2021.102054. Epub Jan. 9, 2021. PMID: 33521604; PMCID: PMC7829205.

Planas, D., et al., Reduced sensitivity of SARS-CoV-2 variant Delta to antibody neutralization. Nature. Aug. 2021;596(7871):276-280. doi: 10.1038/s41586-021-03777-9. Epub Jul. 8, 2021. PMID: 34237773.

(56) References Cited

OTHER PUBLICATIONS

Rauch, S, et al., mRNA-based SARS-CoV-2 vaccine candidate CVnCoV induces high levels of virus-neutralising antibodies and mediates protection in rodents. NPJ Vaccines. Apr. 16, 2021;6(1):57. doi: 10.1038/s41541-021-00311-w. PMID: 33863911; PMCID: PMC8052455.

Sheikh, A, et al., SARS-CoV-2 Delta VOC in Scotland: demographics, risk of hospital admission, and vaccine effectiveness. Lancet. Jun. 26, 2021;397(10293):2461-2462. doi: 10.1016/S0140-6736(21)01358-1. Epub Jun. 14, 2021. PMID: 34139198; PMCID: PMC8201647.

Shen, X, et al., SARS-CoV-2 variant B.1.1.7 is susceptible to neutralizing antibodies elicited by ancestral spike vaccines. Cell Host Microbe. Apr. 14, 2021;29(4):529-539.e3. doi: 10.1016/j.chom.2021.03.002. Epub Mar. 5, 2021. PMID: 33705729; PMCID: PMC7934674.

Szurgot, I., et al., DNA-launched RNA replicon vaccines induce potent anti-SARS-CoV-2 immune responses in mice. 2021 Scientific Reports. 11. 10.1038/s41598-021-82498-5.

Van Der Lubbe, J. E. M., et al., Ad26.COV2.S protects Syrian hamsters against G614 spike variant SARS-CoV-2 and does not enhance respiratory disease. NPJ Vaccines. Mar. 19, 2021;6(1):39. doi: 10.1038/s41541-021-00301-y. PMID: 33741993; PMCID: PMC7979827.

Van Doremalen, N., et al. Immunogenicity of low dose prime-boost vaccination of mRNA vaccine CV07050101 in non-human primates. bioRxiv [Preprint]. Jul. 7, 2021:2021.07.07.451505. doi: 10.1101/2021.07.07.451505. Update in: Viruses. Aug. 19, 2021;13(8): PMID: 34268507; PMCID: PMC8282095.

Van Doremalen, N., et al., ChAdOx1 nCoV-19 vaccine prevents SARS-CoV-2 pneumonia in rhesus macaques. Nature. Oct. 2020;586(7830):578-582. doi: 10.1038/s41586-020-2608-y. Epub Jul. 30, 2020. Erratum in: Nature. Feb. 2021;590(7844):E24. PMID: 32731258; PMCID: PMC8436420.

V'Kovski, P, et al., "Coronavirus biology and replication: implications for SARS-CoV-2". Nature Reviews. (Mar. 2021). Microbiology. 19 (3): 155-170. doi: 10.1038/s41579-020-00468-6. PMC 7592455. PMID 33116300.

Wang, P., et al., Antibody resistance of SARS-CoV-2 variants B.1.351 and B.1.1.7. Nature. May 2021;593(7857):130-135. doi: 10.1038/s41586-021-03398-2. Epub Mar. 8, 2021. PMID: 33684923.

Wang, Z., et al., Naturally enhanced neutralizing breadth against SARS-CoV-2 one year after infection. Nature. Jul. 2021;595(7867):426-431. doi: 10.1038/s41586-021-03696-9. Epub Jun. 14, 2021. PMID: 34126625; PMCID: PMC8277577.

Wu, C, et al. "Analysis of therapeutic targets for SARS-CoV-2 and discovery of potential drugs by computational methods," Acta Pharmaceutica Sinica (May 2020). B. 10 (5): 766-788. doi:10.1016/j.apsb.2020.02.008. PMC 7102550. PMID 32292689, the contents of which are hereby incorporated by reference in their entirety.

Yinda, C. K., et al., Prior aerosol infection with lineage A SARS-CoV-2 variant protects hamsters from disease, but not reinfection with B.1.351 SARS-CoV-2 variant. Emerg Microbes Infect. Dec. 2021;10(1):1284-1292. doi: 10.1080/22221751.2021.1943539. PMID: 34120579; PMCID: PMC8238069.

Yu, Jingyou et al. "DNA vaccine protection against SARS-CoV-2 in rhesus macaques." Science (New York, N.Y.) vol. 369,6505 (2020): 806-811. doi:10.1126/science.abc6284.

Zhang, Y., et al., A second functional furin site in the SARS-CoV-2 spike protein. Emerg Microbes Infect. Dec. 3, 2021:1-35. doi: 10.1080/22221751.2021.2014284. Epub ahead of print. PMID: 34856891.

Zhou, D., et al., Evidence of escape of SARS-CoV-2 variant B.1.351 from natural and vaccine-induced sera. Cell. Apr. 29, 2021;184(9):2348-2361.e6. doi: 10.1016/j.cell.2021.02.037. Epub Feb. 23, 2021. PMID: 33730597; PMCID: PMC7901269.

Zost, S.J., et al., Rapid isolation and profiling of a diverse panel of human monoclonal antibodies targeting the SARS-CoV-2 spike protein. Nat Med. 2020;26(9):1422-1427. PMID: 32651581.

Deo, S., et al. "Evaluation of self-amplifying mRNA platform for protein expression and genetic stability: Implication for mRNA therapies." Biochemical and Biophysical Research Communications 680 (2023): 108-118.

Felgner, Philip L., et al. "Lipofection: a highly efficient, lipid-mediated DNA-transfection procedure." Proceedings of the National Academy of Sciences 84.21 (1987): 7413-7417.

International Search Report issued Jun. 29, 2023 in PCT/US2022/076787.

International Search Report issued Jun. 7, 2023 in PCT/US2022/076304.

Pin, Elisa, et al. "Identification of a Novel Autoimmune Peptide Epitope of Prostein in Prostate Cancer." Journal of Proteome Research 16.1 (2017): 204-216.

\* cited by examiner

COMPOSITIONS AND METHODS FOR DELIVERY OF RNA

This application is a continuation of U.S. application Ser. No. 18/357,280, filed Jul. 24, 2023, which is a continuation of U.S. application Ser. No. 17/839,574, filed Jun. 14, 2022, now U.S. Pat. No. 11,752,218, issued Sep. 12, 2023, which is a continuation of U.S. application Ser. No. 17/702,730, filed Mar. 23, 2022, now U.S. Pat. No. 11,433,142, issued Sep. 6, 2022, which is a continuation of U.S. application Ser. No. 17/523,457, filed Nov. 10, 2021, now U.S. Pat. No. 11,318,213, issued May 3, 2022, which is a continuation of International Application No. PCT/US2021/019103, filed on Feb. 22, 2021, which claims priority to U.S. Provisional Application No. 62/993,307, filed on Mar. 23, 2020, and U.S. Provisional Application No. 63/054,754, filed on Jul. 21, 2020, all of which are herein incorporated by reference in their entirety.

FIELD OF THE INVENTION

The present invention relates generally to RNA delivery. More specifically, this invention relates to nanoparticle-mediated delivery of RNA with a pharmaceutically acceptable nanoparticle that also has the ability to be imaged by use of an inorganic reporter inside the particle.

BACKGROUND

RNA vaccines and therapeutics are a growing area of interest in vaccinology and gene therapy. The use of nucleic acid-encoded antigens as the basis for a vaccine platform has numerous advantages: Purification is relatively streamlined and RNA constructs can be built in days using DNA synthesis technologies followed by RNA transcription and capping. This allows for rapid responses to emerging pathogen threats, pivoting changes in manufacturing to adapt to new circulating strains, or for personalizing therapeutic interventions for a variety of diseases. While these vaccines and therapies show great promise, in some cases they lack full efficacy in human trials and—like protein vaccines—may require a method for enhancing their ability to induce adaptive immune responses.

Several approaches have been tested and are in development, but there remains a need for further and improved nucleic acid vaccines and therapeutics.

SUMMARY

In brief, the present disclosure provides an inorganic compound-based nanoparticle that binds and delivers RNA to a subject in need of treatment. This system has numerous advantages: 1) the RNA is delivered much more efficiently than when the RNA is given on its own or when using other carrier technologies such as nanostructure lipid carrier; 2) the nanoparticles contain a cationic lipid that stabilizes the RNA and protects it from degradation; and 3) the nanoparticles have a reporter element allowing for imaging and tracking the particles in the body.

One aspect of the invention relates to a nanoemulsion composition comprising a plurality of nanoemulsion particles. Each nanoemulsion particle comprises
a hydrophobic core comprising a mixture of a liquid oil and one or more inorganic nanoparticles;
one or more lipids (such as a cationic lipid); and
optionally one or more surfactants.

One aspect of the invention relates to a nanoemulsion composition comprising: (i) a plurality of nanoemulsion particles, and (ii) a bioactive agent complexed with the nanoemulsion particles. Each nanoemulsion particle comprises:
a hydrophobic core comprising a mixture of a liquid oil and one or more inorganic nanoparticles;
one or more lipids (such as a cationic lipid); and
optionally one or more surfactants.

Another aspect of the invention relates to a pharmaceutical composition, comprising the nanoemulsion composition comprising the nanoemulsion particles and the bioactive agent, as described herein, and optionally, a pharmaceutically acceptable carrier or excipient.

Another aspect of the invention relates to a vaccine delivery system comprising the nanoemulsion composition comprising the nanoemulsion particles and the bioactive agent, as described herein, and optionally one or more vaccine adjuvants, wherein the bioactive agent is an antigen or a nucleic acid molecule encoding an antigen.

Another aspect of the invention relates to a method of delivering a bioactive agent to a subject, comprising: administering to the subject the nanoemulsion composition comprising the nanoemulsion particles and the bioactive agent, as described herein.

Another aspect of the invention relates to a method for generating an immune response in a subject, comprising: administering to a subject the nanoemulsion composition comprising the nanoemulsion particles and the bioactive agent, as described herein, and optionally an adjuvant, wherein the bioactive agent is an antigen or a nucleic acid molecule encoding an antigen.

Another aspect of the invention relates to a method of treating or preventing an infection or disease in a subject, comprising: administering to the subject a therapeutically effective amount of the nanoemulsion composition comprising the nanoemulsion particles and the bioactive agent, as described herein, and optionally a pharmaceutically acceptable carrier.

Another aspect of the invention relates to a method of imaging and/or tracking a bioactive agent delivery in a subject, comprising:
administering to the subject the nanoemulsion composition comprising the nanoemulsion particles and the bioactive agent, as described herein, wherein the inorganic nanoparticles contain materials detectable via magnetic resonance imaging, and
detecting the nanoemulsion composition with magnetic resonance imaging.

Another aspect of the invention relates to a method of making a nanoemulsion composition, comprising:
(a) mixing one or more inorganic nanoparticles, a liquid oil, one or more lipids (such as a cationic lipid), and optionally, a hydrophobic surfactant, thereby forming an oil-phase mixture;
(b) mixing the oil-phase mixture with an aqueous solution, optionally containing a hydrophilic surfactant, to form nanoemulsion particles; and
(c) optionally, mixing the nanoemulsion particles with an aqueous solution containing a bioactive agent, thereby complexing the bioactive agent with the nanoemulsion particles.

BRIEF DESCRIPTION OF THE DRAWINGS

FIG. 1A shows LIONs labeled as 79-004 produced in Example 1. FIG. 1B shows LIONs labeled as 79-006-A produced in Example 1. FIG. 1C shows LIONs labeled as 79-006-B produced in Example 1.

FIG. 6F shows anti-SOSIP IgG responses in rabbit kits at time of delivery. A minimum of two rabbit kits from each litter per treatment group were euthanized to evaluate in utero antibody transfer. FIG. 6G shows the XY plot demonstrating a positive correlation (Pearson r=0.94) between antibody levels in rabbit does and corresponding rabbit kits.

FIG. 7A shows that codon-optimized full length spike (S) open reading frame, including the S1-, S2-, trans-membrane-(TM), and cytoplasmic-(CD) domains, corresponding to positions 21,536 to 25,384 in SARS-CoV-2 isolate Wuhan-Hu-1 (GenBank: MN908947.3), fused to a c-terminal v5 epitope tag, was cloned into an alphavirus replicon encoding the 4 nonstructural protein (nsP1-4) genes of Venezuelan equine encephalitis virus, strain TC-83. FIGS. 7B and 7C show the analysis results of cells, 24 hours later following the transfection of repRNA-COV2S into BHK cells, by anti-v5 immunofluorescence (FIG. 7B) and western blot (FIG. 7C), using either convalescent human serum or anti-v5 for immunodetection. Recombinant SARS-CoV2 spike protein (rCoV2-Spike) and repRNA-GFP were used as positive and negative controls, respectively. Data in FIGS. 7B and 7C are representative of two independent experiments.

FIG. 8A is a graphical representation of an exemplary LION and its formation of vaccine complex after mixing with repRNA. FIG. 8B is a graph showing the time evolution of LION particle size, measured by dynamic light scattering (DLS), after storage at 4° C., 25° C. and 42° C. FIG. 8C is a graph showing the confirmation of a complex formation by a shift in size distribution, after mixing LION and repRNA. FIG. 8D shows the gel electrophoresis analysis of triplicate preparations of repRNA extracted from LION, following a concentrated RNase challenge, illustrating substantial protection relative to a triplicate preparation of a dose-matched naked RNA, following a RNAse challenge. FIG. 8E shows the gel electrophoresis of repRNA extracted by phenol-chloroform treatment.

FIG. 9A shows the results of anti-S IgG concentrations in the serum of the C57BL/6 mice, determined by enzyme linked immunosorbent assay (ELISA). FIG. 9B shows the 50% inhibitory concentrations (IC50) in the serum of the C57BL/6 mice, determined by pseudovirus (SARS-CoV-2 Wuhan-Hu-1 pseudotype) neutralization assays. FIG. 9C and FIG. 9D show the anti-S IgG1 and IgG2c concentrations (FIG. 9C) and the IgG2c:IgG1 concentration ratio (FIG. 9D) in the serum of the C57BL/6 mice, determined by ELISA. On day 28, mice received a booster immunization, and 12 days later, the spleens and lungs were harvested. FIGS. 9E and 9F show the results of the IFN-γ responses in spleen cells (FIG. 9E) and in lung cells (FIG. 9F), measured by enzyme-linked immune absorbent spot (ELISpot), following 18-hour stimulation with 10 peptide pools encompassing the S protein and consisting of 15-mers overlapping by 11 amino acids. Data in FIG. 9A, FIG. 9C, and FIG. 9D are representative of three independent experiments, while data in FIG. 9B, FIG. 9E, and FIG. 9F were from a single experiment. All data are represented as individual values as well as mean±s.d. *$p<0.05$, as determined by one-way ANOVA with Tukey's multiple comparison test.

FIGS. 10A, 10B, and 10C show the results of the anti-S IgG concentration (FIG. 10A), IgG1 concentration and IgG2a concentrations (FIG. 10B), and the IgG2a:IgG1 concentration ratios (FIG. 10C) in the serum of the aged BALB/C mice, determined by ELISA. Data in 17-, 8-, and 2-month old BALB/Cs were from a single experiment, and data for the 2-month old BALB/Cs were replicated in a second experiment. All data are represented as individual values as well as mean±s.d. *$p<0.05$, as determined by one-way ANOVA with Tukey's multiple comparison test between the 17-month old animals and either the 8- or 2-month old animals.

FIG. 11A shows the dosage regime, in which pigtail macaques were vaccinated with 250 µg (n=3) or with 50 µg (n=2) repRNA-CoV2-S complex via the intramuscular route, with the blood being collected on days 10, 14, 28, and 42; the 50 µg group received a boost vaccination on day 28, with the blood being collected 14 days later. FIG. 11B shows the results of the serum anti-S IgG ELISAs performed on the post-immunization samples, against the baseline established by the pre-immunization blood draws. FIG. 11C shows the results of the mean 50% inhibitory concentrations (IC50) of each sample, determined by the pseudovirus (SARS-CoV-2 Wuhan-Hu-1 pseudotype) neutralization assays, against the baseline established by the pre-immunization blood draws. FIG. 11D shows that 80% plaque-reduction neutralizing antibody titers (PRNT$_{80}$) against SARS-CoV2/WA/2020 isolate were measured at days 28 and 42 alongside sera from 7 convalescent human samples collected from confirmed COVID-19 patients. The experiment was performed once. Each line in FIG. 11B and FIG. 11C are representative of each individual animal. Data in FIG. 11D are reported as individual values as well as mean±s.d. *$p<0.05$, as determined by students t-test comparing 250 µg groups at days 14 and 28. There was no significant difference (ns) between mean PRNT$_{80}$ titers in all 5 animals at day 42 and titers in sera from 7 convalescent humans, as measured by Mann-Whitney U test.

FIG. 14A shows the gel electrophoresis analysis of PAMP-LION complexes at various N:P complexing ratio (0.04, 0.2, 1, 5, and 25, respectively) run on an RNA gel and was assessed for free RNA. FIG. 14B shows the gel electrophoresis analysis of PAMP-LION complexes, following a challenge with RNase A, as compared to naked PAMP (unformulated PAMP). RNA was extracted from LION and run on an agarose gel to assess RNA degradation.

DETAILED DESCRIPTION OF THE INVENTION

Figure 1A:
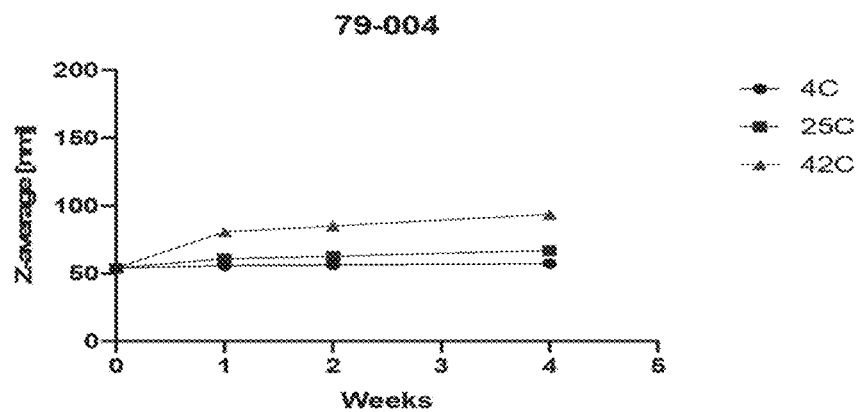
FIGS. 1A-1C show the particle size and stability of three exemplary lipid inorganic nanoparticles (LION) formulations at various temperatures as a function time.

This disclosure provides for use of Lipid InOrganic Nanoparticles (LIONs) as carriers of RNA. In particular, a solid inorganic core in a lipid matrix with a charged coating in a buffer is disclosed. The use of these nanoparticles has numerous advantages: RNA can be complexed independent of the particles, and the particle can be designed to have magnetic signals, such as useable for MRI or other imaging techniques. RNA is protected by the particles and they drive expression of numerous types of protein including antigens off of the protected RNA when given to cells or a living being.

One aspect of the invention relates to a nanoemulsion composition comprising a plurality of nanoemulsion particles. Each nanoemulsion particle comprises
    a hydrophobic core comprising a mixture of a liquid oil and one or more inorganic nanoparticles;
    one or more lipids (e.g., a cationic lipid); and
    optionally one or more surfactants.

Another aspect of the invention relates to a nanoemulsion composition comprising: (i) a plurality of nanoemulsion particles, and (ii) a bioactive agent complexed with the nanoemulsion particles. Each nanoemulsion particle comprises:
    a hydrophobic core comprising a mixture of a liquid oil and one or more inorganic nanoparticles;
    one or more lipids (e.g., a cationic lipid); and
    optionally one or more surfactants.

The Nanoemulsion Particles

The nanoemulsion particle has a hydrophobic core comprising a mixture of a liquid oil and one or more inorganic solid nanoparticles. The nanoemulsion particle can also be referred to herein as Lipid InOrganic Nanoparticles (LIONs).

The liquid oil is mixed with the one or more inorganic nanoparticles to form a hydrophobic core. The liquid oil is typically metabolizable. Suitable liquid oil can be a vegetable oil, animal oil, or synthetically prepared oil.

In some embodiments, the liquid oil is a fish oil. In some embodiments, the liquid oil is a naturally occurring or synthetic terpenoid.

In some embodiments, the liquid oil is squalene, triglyceride (such as capric/caprylic triglyceride or myristic acid triglyceride), vitamin E, lauroyl polyoxylglyceride, monoacylglycerol, soy lecithin, sunflower oil, soybean oil, olive oil, grapeseed oil, or a combination thereof. In one embodiment, the liquid oil is squalene, triglyceride (such as capric/caprylic triglyceride or myristic acid triglyceride), vitamin E, lauroyl polyoxylglyceride, monoacylglycerol, soy lecithin, or a combination thereof. In one embodiment, the liquid oil is squalene, triglyceride (such as capric/caprylic triglyceride or myristic acid triglyceride), sunflower oil, soybean oil, olive oil, grapeseed oil, or a combination thereof.

In some embodiments, the liquid oil is squalene (either naturally occurring or synthetic, optionally in combination with any of the above listed liquid oils.

The inorganic nanoparticles may be formed from one or more same or different metals (any metals including transition metal), such as from metal salts, metal oxides, metal hydroxides, and metal phosphates. Examples include silicon dioxide ($SiO_2$), iron oxides ($Fe_3O_4$, $Fe_2O_3$, FeO, or combinations thereof), aluminum oxide ($Al_2O_3$), aluminum oxyhydroxide (AlO(OH)), aluminum hydroxyphosphate ($Al(OH)_x(PO_4)_y$), calcium phosphate ($Ca_3(PO_4)_2$), calcium hydroxyapatite ($Ca_{10}(PO_4)_6(OH)_2$), iron gluconate, or iron sulfate.

In some embodiments, the inorganic solid nanoparticle is a metal oxide, such as a transition metal oxide. In one embodiment, the inorganic solid nanoparticle is an iron oxide, for instance, magnetite ($Fe_3O_4$), maghemite ($\gamma$-$Fe_2O_3$), wüstite (FeO), hematite ($\alpha$-$Fe_2O_3$), or combinations thereof.

In some embodiments, the inorganic solid nanoparticle is a metal hydroxide, such as an aluminum hydroxide or aluminum oxyhydroxide.

The inorganic solid nanoparticle may contain a reporter element detectable via imaging methods to allow for imaging and tracking the resulting nanoemulsion particles in the body. For instance, the inorganic solid nanoparticle may contain a reporter element detectable via magnetic resonance imaging (MRI), such as a paramagnetic, superparamagnetic, ferrimagnetic or ferromagnetic compound. Exemplary inorganic solid nanoparticle materials that are MRI-detectable are iron oxides, iron gluconates, and iron sulfates.

The inorganic solid nanoparticle typically has an average diameter (number weighted average diameter) ranging from about 3 nm to about 50 nm. For instance, the inorganic solid nanoparticle can have an average diameter of about 5 nm, about 10 nm, about 15 nm, about 20 nm, about 25 nm, about 30 nm, about 35 nm, about 40 nm, about 45 nm, or about 50 nm.

The inorganic solid nanoparticle may be surface modified before mixing with the liquid oil. For instance, if the surface of the inorganic solid nanoparticle is hydrophilic, the inorganic solid nanoparticle may be coated with hydrophobic molecules (or surfactants) to facilitate the miscibility of the inorganic solid nanoparticle with the liquid oil in the "oil" phase of the nanoemulsion particle. Phosphate-terminated lipids (such as phosphatidylated lipids), phosphorous-terminated surfactants, carboxylate-terminated surfactants, sulfate-terminated surfactants, or amine-terminated surfactants can be used for surface modification of the inorganic solid nanoparticle. Typical phosphate-terminated lipids or phosphorous-terminated surfactants are trioctylphosphine oxide (TOPO) or distearyl phosphatidic acid (DSPA). Typical sulfate-terminated surfactants include but not limited to sodium dodecyl sulfate (SDS). Typical carboxylate-terminated surfactants include oleic acid. Typical amine terminated surfactants include oleylamine.

In one embodiment, the inorganic solid nanoparticle is a metal oxide such as an iron oxide, and a surfactant, such as oleic acid, oleylamine, SDS, DSPA, or TOPO, is used to coat the inorganic solid nanoparticle, before it is mixed with the liquid oil to form the hydrophobic core.

In one embodiment, the inorganic solid nanoparticle is a metal hydroxide, such as an aluminum hydroxide or aluminum oxyhydroxide, and a phosphate-terminated lipid or a surfactant, such as oleic acid, oleylamine, SDS, TOPO or DSPA is used to coat the inorganic solid nanoparticle, before it is mixed with the liquid oil to form the hydrophobic core.

The lipids used to form nanoemulsion particles can be cationic lipids, anionic lipids, neutral lipids, or mixtures thereof.

In some embodiments, the lipids used are cationic lipids. For example, positively charged lipids that can have favorable interactions with negatively charged bioactive agent (such as DNAs or RNAs) may be used in the nanoemulsion composition. Suitable cationic lipids include 1,2-dioleoyloxy-3-(trimethylammonium)propane (DOTAP); 3β-[N-(N',N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0)trimethyl ammonium propane (DPTAP); distearoyltrimethylammonium propane (DSTAP); N-[1-(2,3-dioleyloxy)propyl]-N,N,N-trimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLinDMA); 1,1'-((2-(4-(2-((2-(bis(2-hydroxydodecyl)amino)ethyl) (2-hydroxydodecyl) amino)ethyl)piperazin-1-yl)ethyl)azanediyl)bis(dodecan-2-ol) (C12-200); and combinations thereof. A typical cationic lipid is DOTAP.

Other examples for suitable lipids include, but are not limited to, the phosphatidylcholines (PCs), such as distearoylphosphatidylcholine (DSPC), dioleoyl phosphatidylcholine (DOPC), 1-palmitoyl-2-oleoylphosphatidylcholine (POPC), dipalmitoylphosphatidylcholine (DPPC), dipalmitoylphosphatidylcholine (DMPC), etc; phosphatidylethanolamines (PEs), such as 1,2-distearoyl-sn-glycero-3-phosphoethanolamine (DSPE), dioleoylphosphatidylethanolamine (DOPE), etc.; phosphatidylglycerol (PGs); and PEGylated lipids including PEGylated version of any of the above lipids (e.g., DSPE-PEGs).

The nanoemulsion particle can further contain one or more surfactants, which can be a hydrophobic surfactant or a hydrophilic surfactant. In some embodiments, the nanoemulsion particle further comprises a hydrophobic surfactant. In some embodiments, the nanoemulsion particle further comprises a hydrophilic surfactant. In one embodiment, the nanoemulsion particle further comprises a hydrophobic surfactant and a hydrophilic surfactant.

Suitable hydrophobic surfactants include those having a hydrophilic-lipophilic balance (HLB) value of 10 or less, for instance, 5 or less, from 1 to 5, or from 4 to 5. An exemplary hydrophobic surfactant is a sorbitan ester (such as sorbitan monoester or sorbitan trimester). For instance, the hydrophobic surfactant can be a sorbitan ester having a HLB value from 1 to 5, or from 4 to 5.

In some embodiments, the hydrophobic surfactant is a sorbitan monoester or a sorbitan triester. Exemplary sorbitan monoesters include sorbitan monostearate and sorbitan monooleate. Exemplary sorbitan triesters include sorbitan tristearate and sorbitan trioleate.

Suitable hydrophilic surfactants include those polyethylene oxide-based surfactants, for instance, a polyoxyethylene sorbitan ester (polysorbate). In some embodiments, the hydrophilic surfactant is a polysorbate. Exemplary polysorbates are polysorbate 80 (polyoxyethylene sorbitan monooleate, or Tween 80), polysorbate 60 (polyoxyethylene sorbitan monostearate, or Tween 60), polysorbate 40 (polyoxyethylene sorbitan monopalmitate, or Tween 40), and polysorbate 20 (polyoxyethylene sorbitan monolaurate, or Tween 20). In one embodiment, the hydrophilic surfactant is polysorbate 80.

The nanoemulsion particle can have an oil-to-surfactant molar ratio ranging from about 0.1:1 to about 20:1, from about 0.5:1 to about 12:1, from about 0.5:1 to about 9:1, from about 0.5:1 to about 5:1, from about 0.5:1 to about 3:1, or from about 0.5:1 to about 1:1.

The nanoemulsion particle can have a hydrophilic surfactant-to-lipid (e.g., cationic lipid) ratio ranging from about 0.1:1 to about 2:1, from about 0.2:1 to about 1.5:1, from about 0.3:1 to about 1:1, from about 0.5:1 to about 1:1, or from about 0.6:1 to about 1:1.

The nanoemulsion particle can have a hydrophobic surfactant-to-lipid (e.g., cationic lipid) ratio ranging from about 0.1:1 to about 5:1, from about 0.2:1 to about 3:1, from about 0.3:1 to about 2:1, from about 0.5:1 to about 2:1, or from about 1:1 to about 2:1.

The nanoemulsion particle can comprise from about 0.2% to about 40% w/v liquid oil, from about 0.001% to about 10% w/v inorganic solid nanoparticle, from about 0.2% to about 10% w/v lipid (e.g., cationic lipid), from about 0.25% to about 5% w/v hydrophobic surfactant (e.g., sorbitan ester), and from about 0.5% to about 10% w/v hydrophilic surfactant.

In certain embodiments, the nanoemulsion particle comprises:
  a hydrophobic core comprising a mixture of
    one or more inorganic nanoparticles containing at least one metal oxide nanoparticle optionally coated with a phosphate-terminated lipid, a phosphorous-terminated surfactant, a carboxylate-terminated surfactant, a sulfate-terminated surfactant, or an amine-terminated surfactant, and
    a liquid oil containing naturally occurring or synthetic squalene;
  a cationic lipid comprising DOTAP;
  a hydrophobic surfactant comprising a sorbitan ester selected from the group consisting of sorbitan monostearate, sorbitan monooleate, and sorbitan trioleate; and
  a hydrophilic surfactant comprising a polysorbate.

In one embodiment, the nanoemulsion particle comprises:
  a hydrophobic core comprising a mixture of
    one or more inorganic nanoparticles containing iron oxide nanoparticles, and
    a liquid oil containing naturally occurring or synthetic squalene;
  the cationic lipid DOTAP;
  a hydrophobic surfactant comprising sorbitan monostearate; and
  a hydrophilic surfactant comprising polysorbate 80.

In this LION composition, the LION particle can comprise from about 0.2% to about 40% w/v squalene, from about 0.001% to about 10% w/v iron oxide nanoparticles, from about 0.2% to about 10% w/v DOTAP, from about 0.25% to about 5% w/v sorbitan monostearate, and from about 0.5% to about 10% w/v polysorbate 80.

In one embodiment, the LION particle comprises from about 2% to about 6% w/v squalene, from about 0.01% to about 1% w/v iron oxide nanoparticles, from about 0.2% to about 1% w/v DOTAP, from about 0.25% to about 1% w/v sorbitan monostearate, and from about 0.5%) to about 5% w/v polysorbate 80.

In certain embodiments, the nanoemulsion particle comprises:
  a hydrophobic core comprising a mixture of
    one or more inorganic nanoparticles containing at least one metal hydroxide or oxyhydroxide nanoparticle optionally coated with a phosphate-terminated lipid, a phosphorous-terminated surfactant, a carboxylate-terminated surfactant, a sulfate-terminated surfactant, or an amine-terminated surfactant, and
    a liquid oil containing naturally occurring or synthetic squalene;
  a cationic lipid comprising DOTAP;
  a hydrophobic surfactant comprising a sorbitan ester selected from the group consisting of sorbitan monostearate, sorbitan monooleate, and sorbitan trioleate; and
  a hydrophilic surfactant comprising a polysorbate.

In one embodiment, the nanoemulsion particle comprises:
  a hydrophobic core comprising a mixture of
    one or more inorganic nanoparticles containing aluminum hydroxide or aluminum oxyhydroxide nanoparticles optionally coated with TOPO, and
    a liquid oil containing naturally occurring or synthetic squalene;
  the cationic lipid DOTAP;
  a hydrophobic surfactant comprising sorbitan monostearate; and
  a hydrophilic surfactant comprising polysorbate 80.

In this LION composition, the LION particle can comprise from about 0.2% to about 40% w/v squalene, from about 0.001% to about 10% w/v aluminum hydroxide or aluminum oxyhydroxide nanoparticles, from about 0.2% to about 10% w/v DOTAP, from about 0.25% to about 5% w/v sorbitan monostearate, and from about 0.5% to about 10% w/v polysorbate 80.

In one embodiment, the LION particle comprises from about 2% to about 6% w/v squalene, from about 0.01% to about 1% w/v aluminum hydroxide or aluminum oxyhydroxide nanoparticles, from about 0.2% to about 1% w/v DOTAP, from about 0.25% to about 1% w/v sorbitan monostearate, and from about 0.5%) to about 5% w/v polysorbate 80.

Nanoparticles and nanoemulsions have been described in the literature and the terms are used herein to refer to those particles having a size less than 1000 nanometers.

The nanoemulsion particle (LION) typically has an average diameter (z-average hydrodynamic diameter, measured by dynamic light scattering) ranging from about 20 nm to about 200 nm. In some embodiments, the z-average diameter of the LION particle ranges from about 20 nm to about 150 nm, from about 20 nm to about 100 nm, from about 20 nm to about 80 nm, from about 20 nm to about 60 nm. In some embodiments, the z-average diameter of the LION particle ranges from about 40 nm to about 200 nm, from about 40 nm to about 150 nm, from about 40 nm to about 100 nm, from about 40 nm to about 90 nm, from about 40 nm to about 80 nm, or from about 40 nm to about 60 nm. In one embodiment, the z-average diameter of the LION particle is from about 40 nm to about 80 nm. In one embodiment, the z-average diameter of the LION particle is from about 40 nm to about 60 nm.

The average polydispersity index (PDI) of the nanoemulsion particles (LIONs) can range from about 0.1 to about 0.5. For instance, the average PDI of the LION particles can range from about 0.2 to about 0.5, from about 0.1 to about 0.4, from about 0.2 to about 0.4, from about 0.2 to about 0.3, or from about 0.1 to about 0.3.

The LION-Bioactive Agent Complex.

The nanoemulsion composition can further contain a bioactive agent that is associated/complexed with the nanoemulsion particles (LIONs). The bioactive agent may be associated/complexed with the nanoemulsion particles via non-covalent interactions or via reversible covalent interactions.

The bioactive agent can be a protein or a bioactive agent encoding a protein. For instance, the bioactive agent can be a protein antigen or a bioactive agent encoding a protein antigen. The antigen can be derived from, or immunologically cross-reactive with, an infectious pathogen and/or an epitope, biomolecule, cell or tissue that is associated with infection, cancer, or autoimmune disease.

In some embodiments, the bioactive agent is a nucleic acid, such as a RNA or DNA. A variety of RNAs can be associated with the LION particles for delivery, including RNAs that modulate innate immune responses, RNAs that encode proteins or antigens, silencing RNAs, microRNAs, tRNAs, self-replicating RNAs, etc.

In one embodiment, the bioactive agent is mRNA. In one embodiment, the bioactive agent is oncolytic viral RNA. In one embodiment, the bioactive agent is a replicon RNA.

In certain embodiments, the bioactive agent is an RNA encoding an antigen or an antibody. The antigen may be derived from a bacterial disease, a viral disease, a protozoan disease, a non-communicable disease, cancer, or an autoimmune disease. In certain embodiments, the antigen is derived from a RNA virus, such as a hepatitis virus, a corona virus, a mosquito-borne virus (e.g., Venezuelan equine encephalitis (VEE) virus, or flavivirus such as ZIKV virus), or a HIV virus. In certain embodiments, the antigen is derived from a corona virus selected from the group consisting a MERS virus and a SARS virus (such as SARS-CoV-2).

In certain embodiments, the bioactive agent is a non-coding RNA.

The bioactive agent can also be an adjuvant. Suitable adjuvants include a TLR agonist, a RIG-I agonist, a saponin, a peptide, a protein, a carbohydrate, a carbohydrate polymer, a conjugated carbohydrate, a whole viral particle, a virus-like particle, viral fragments, cellular fragments, and combinations thereof.

In certain embodiments, the adjuvant is a TLR agonist or a RIG-I agonist. Exemplary TLR agonists include a TLR2, TLR3, TLR4, TLR7, TLR8, or TLR9 agonist. A typical TLR agonist is a TLR3 agonist, such as RIBOXXOL, poly(I:C), or Hiltonol®.

In certain embodiments, the bioactive agent is a double-stranded RNA.

In certain embodiments, the bioactive agent is an RNA that is an immune stimulator. The immune stimulators can be a TLR3 agonist (e.g., a TLR2, TLR3, TLR4, TLR7, TLR8, or TLR9 agonist) or a RIG-I agonist (e.g., a PAMP). A typical TLR agonist is a TLR3 agonist, such as RIBOXXOL, poly(I:C), or Hiltonol®.

As an alternative to, or in addition to the delivery of RNAs as antigens, combinations can be used, e.g., RNA antigens combined with RNAs that stimulate innate immune responses, or RNAs that launch oncolytic viruses, or live-attenuated viruses.

In certain embodiments, the bioactive agent in the nanoemulsion composition can comprise a combination of RNA-encoded antigens with another RNA that can stimulate innate immune responses or can launch oncolytic viruses or live-attenuated viruses. Alternatively, the nanoemulsion composition containing RNA-encoded antigens can be combined with a formulation that contains another RNA that can stimulate innate immune responses or can launch oncolytic viruses or live-attenuated viruses.

In the nanoemulsion composition, the molar ratio of (i) the nanoemulsion particles (LIONs) to (ii) the bioactive agent can be characterized by the nitrogen-to-phosphate molar ratio, which can range from about 0.01:1 to about 1000:1, for instance, from about 0.2:1 to about 500:1, from about 0.5:1 to about 150:1, from about 1:1 to about 150:1, from about 1:1 to about 125:1, from about 1:1 to about 100:1, from about 1:1 to about 50:1, from about 1:1 to about 50:1, from about 5:1 to about 50:1, from about 5:1 to about 25:1, or from about 10:1 to about 20:1. A molar ratio of the nanoemulsion particles (LIONs) to the bioactive agent can be chosen to increase the delivery efficiency of the bioactive agent, increase the ability of the bioactive agent-carrying nanoemulsion composition to elicit an immune response to the antigen, increase the ability of the bioactive agent-carrying nanoemulsion composition to elicit the production of antibody titers to the antigen in a subject. In certain embodiments, the molar ratio of the nanoemulsion particles (LIONs) to the bioactive agent, characterized by the nitrogen-to-phosphate (N:P) molar ratio, ranges from about 1:1 to about 150:1, from about 5:1 to about 25:1, or from about 10:1 to about 20:1. In one embodiment, the N:P molar ratio of the nanoemulsion composition is about 15:1.

By complexing with the bioactive agent, the nanoemulsion composition can deliver the bioactive agent to a cell. The cell can be in a subject in need. For instance, when the bioactive agent is a protein antigen or encodes a protein antigen, the nanoemulsion composition carrying the bioactive agent can elicit an immune response in the subject against the antigen. The nanoemulsion composition may do so by eliciting antibody titers to the antigen in the subject, for instance, by inducing neutralizing antibody titers in the subject.

In one embodiment, the nanoemulsion composition containing the LIONs, when administered in an effective amount to the subject, can elicit an immune response to the antigen equal to or greater than the immune response elicited when the bioactive agent is administered to the subject without the LIONs.

Without being bound by theory, the hydrophobic surfactants in the nanoemulsion composition may contribute to increase the ability of the nanoemulsion composition to deliver a bioactive agent to the cell or to increase the ability of the nanoemulsion composition carrying a bioactive agent to elicit an immune response in the subject against the antigen (when the bioactive agent is a protein antigen or encodes a protein antigen). For instance, the hydrophobic surfactants in the nanoemulsion composition may contribute to increase the ability of the nanoemulsion composition carrying a bioactive agent In one embodiment, the hydrophobic surfactant is a sorbitan ester and is present in an amount sufficient to increase the ability of the nanoemulsion composition to deliver a bioactive agent to the cell (or to the subject), as compared to a same nanoemulsion composition, but without the sorbitan ester hydrophobic surfactant.

In one embodiment, the hydrophobic surfactant is a sorbitan ester and is present in an amount sufficient to increase the ability of the bioactive agent-carrying nanoemulsion composition to elicit an immune response to the antigen, as compared to a same nanoemulsion composition, but without the sorbitan ester hydrophobic surfactant.

In one embodiment, the hydrophobic surfactant is a sorbitan ester and, when administered in an effective amount to the subject, the nanoemulsion composition elicits antibody titers to the antigen at a higher level than the antibody titers elicited when a same nanoemulsion composition (but without the sorbitan ester hydrophobic surfactant) is administered to the subject.

In one embodiment, the hydrophobic surfactant is a sorbitan ester and, when administered in an effective amount to the subject, the nanoemulsion composition induces neutralizing antibody titers in the subject at a higher level than the neutralizing antibody titers induced when a same nanoemulsion composition (but without the sorbitan ester hydrophobic surfactant) is administered to the subject.

Preparing the Nanoemulsion Composition

Another aspect of the invention relates to a method of making a nanoemulsion composition, comprising:
  (a) mixing one or more inorganic nanoparticles, a liquid oil, one or more lipids (e.g., a cationic lipid), and optionally, a hydrophobic surfactant, thereby forming an oil phase mixture; and
  (b) mixing the oil-phase mixture with an aqueous solution, optionally containing a hydrophilic surfactant, to form nanoemulsion particles.

The method can further comprise step (c) mixing the nanoemulsion particles with an aqueous solution containing a bioactive agent, thereby complexing the bioactive agent with the nanoemulsion particles.

The bioactive agent may be associated/complexed with the nanoemulsion particles via non-covalent interactions or via reversible covalent interactions.

All above descriptions and all embodiments regarding the nanoemulsion composition, nanoemulsion particles (including liquid oil, inorganic nanoparticles, lipid such as cationic lipid, hydrophobic surfactant, and hydrophilic surfactant), and bioactive agents discussed above in the aspect of the invention relating to the nanoemulsion composition comprising the nanoemulsion particles and in the aspect of the invention relating to the nanoemulsion composition comprising the nanoemulsion particles and a bioactive agent are applicable to this aspect of the invention.

The resulting nanoemulsion composition can be prepared in a diluted or concentrated form.

In certain embodiments, the nanoemulsion composition may be diluted (by any suitable buffer solutions) to about 1 to about 200 fold, for instance, about 1 to about 100 fold, about 2 to about 50 fold, about 2 to about 30 fold, about 2 to about 20 fold, about 2 to about 10 fold, about 2 to about 5 fold. In one embodiments, the nanoemulsion composition is diluted in 2 fold.

In certain embodiments, the nanoemulsion composition may be concentrated about 1 to about 100 fold, for instance, about 2 to about 50 fold, about 2 to about 30 fold, about 2 to about 20 fold, about 2 to about 10 fold, about 2 to about 5 fold.

The nanoemulsion composition can have a loading capacity for the bioactive agent (e.g., a nucleic acid such as RNA or DNA) of at least about 100 µg/ml.

The dosage level of the bioactive agent (e.g., a nucleic acid such as RNA or DNA) in the nanoemulsion composition can range from about 0.001 µg/ml to about 1000 µg/ml, for instance, from about 0.002 µg/ml to about 500 µg/ml, from about 1 µg/ml to about 500 µg/ml, from about 2 µg/ml to about 400 µg/ml, from about 40 µg/ml to about 400 µg/ml, or from about 10 µg/ml to about 250 µg/ml.

Use of the Nanoemulsion Composition

Various aspects the invention also relate to the use of the nanoemulsion composition comprising the nanoemulsion particles and the bioactive agent, including, for instance, in a pharmaceutical composition, as a vaccine delivery system, in delivering a bioactive agent to a cell or a subject, generating an immune response in a subject, and treating a subject in need.

In one aspect, the invention provides a pharmaceutical composition comprising the nanoemulsion composition comprising the nanoemulsion particles and the bioactive agent, as described herein. Optionally, the pharmaceutical composition can comprise a pharmaceutically acceptable carrier or excipient. As used herein the term "pharmaceutically acceptable carrier or excipient" includes solvents, dispersion media, coatings, antibacterial and antifungal agents, isotonic and absorption delaying agents, etc., compatible with pharmaceutical administration.

In another aspect, the invention provides a vaccine delivery system comprising the nanoemulsion composition comprising the nanoemulsion particles and the bioactive agent, as described herein, and optionally one or more vaccine adjuvant, wherein the bioactive agent is an antigen or a nucleic acid molecule encoding an antigen.

All above descriptions and all embodiments regarding the nanoemulsion composition, nanoemulsion particles (including liquid oil, inorganic nanoparticles, lipid such as cationic lipid, hydrophobic surfactant, and hydrophilic surfactant), bioactive agents, and preparation of the nanoemulsion composition discussed above in the aspect of the invention relating to the nanoemulsion composition comprising the nanoemulsion particles, in the aspect of the invention relating to the nanoemulsion composition comprising the nanoemulsion particles and a bioactive agent, and in the aspect of the invention relating to the method of making a nanoemulsion composition are applicable to these two aspects of the invention relating to the pharmaceutical composition and the vaccine delivery system.

The pharmaceutical composition and the vaccine delivery system can be formulated for various administrative routes, including oral administration, or parenteral administration, such as intravenous, intramuscular, intradermal, subcutaneous, intraocular, intranasal, pulmonary (e.g., by inhalation) intraperitoneal, or intrarectal administration.

In one embodiment, the delivery route is pulmonary delivery (e.g., to lung), which can be achieved by different approaches, including the use of nebulized, aerosolized, micellular, or dry powder-based formulations. In one embodiment, the pharmaceutical composition or the vaccine delivery system are formulated to be administrated in liquid nebulizers, aerosol-based inhalers, and/or dry powder dispersion devices.

One aspect of the invention relates to a method of delivering a bioactive agent to a cell, comprising: contacting the cell with the nanoemulsion composition comprising the nanoemulsion particles and the bioactive agent, as described herein.

One aspect of the invention relates to a method of delivering a bioactive agent to a subject, comprising: administering to the subject the nanoemulsion composition comprising the nanoemulsion particles and the bioactive agent, as described herein.

All above descriptions and all embodiments regarding the nanoemulsion composition, nanoemulsion particles (including liquid oil, inorganic nanoparticles, lipid such as cationic lipid, hydrophobic surfactant, and hydrophilic surfactant), bioactive agents, and preparation of the nanoemulsion composition discussed above in the aspect of the invention relating to the nanoemulsion composition comprising the nanoemulsion particles, in the aspect of the invention relating to the nanoemulsion composition comprising the nanoemulsion particles and a bioactive agent, and in the aspect of the invention relating to the method of making a nanoemulsion composition are applicable to these two aspects of the invention relating to the method of delivering a bioactive agent.

The ability and efficiency of the delivery of the bioactive agent by the nanoemulsion particles to a cell or a subject can be controlled by adjusting the components of the nanoemulsion particles, selecting the molar ratio of the nanoemulsion particles (LIONs) to the bioactive agent, and/or selecting the dosage of the bioactive agent, as described herein.

One aspect of the invention relates to a method for generating an immune response in a subject, comprising: administering to a subject the nanoemulsion composition comprising the nanoemulsion particles and the bioactive agent, as described herein, and optionally an adjuvant, wherein the bioactive agent is an antigen or a nucleic acid molecule encoding an antigen.

One aspect of the invention relates to a method of generating an immune response in a subject, comprising:
  (a) administering to the subject a therapeutically effective amount of an oncolytic virus encoding a protein antigen, and;
  (b) administering to the subject a therapeutically effective amount of the nanoemulsion composition comprising the nanoemulsion particles and the bioactive agent, as described herein, and optionally an adjuvant, wherein the bioactive agent is the protein antigen or a nucleic acid molecule encoding the protein antigen.

All above descriptions and all embodiments regarding the nanoemulsion composition, nanoemulsion particles (including liquid oil, inorganic nanoparticles, lipid such as cationic lipid, hydrophobic surfactant, and hydrophilic surfactant), bioactive agents, preparation of the nanoemulsion composition, pharmaceutical composition, and vaccine delivery system discussed above in the aspects of the invention relating to the nanoemulsion composition comprising the nanoemulsion particles, relating to the nanoemulsion composition comprising the nanoemulsion particles and a bioactive agent, relating to the method of making a nanoemulsion composition, relating to the pharmaceutical composition, and relating to the vaccine delivery system are applicable to these two aspects of the invention relating to the method of generating an immune response.

The administrative routes in these methods are the same as those described above for administrating the pharmaceutical composition and the vaccine delivery system.

The administration of (a) step and the administration of (b) step can occur simultaneously. Alternatively, the administration of (a) step and the administration of (b) step can occur at least 1 week, at least 2 weeks, at least 3 weeks, at least 1 month, at least 6 weeks, at least two months, at least three months, at least 6 months, or at least 1 year apart.

One aspect of the invention also relates to a method of treating or preventing an infection or disease in a subject, comprising: administering to the subject a therapeutically effective amount of the nanoemulsion composition comprising the nanoemulsion particles and the bioactive agent, as described herein, and optionally a pharmaceutically acceptable carrier.

All above descriptions and all embodiments regarding the nanoemulsion composition, nanoemulsion particles (including liquid oil, inorganic nanoparticles, lipid such as cationic lipid, hydrophobic surfactant, and hydrophilic surfactant), bioactive agents, preparation of the nanoemulsion composition, pharmaceutical composition, and vaccine delivery system discussed above in the aspects of the invention relating to the nanoemulsion composition comprising the nanoemulsion particles, relating to the nanoemulsion composition comprising the nanoemulsion particles and a bioactive agent, relating to the method of making a nanoemulsion composition, relating to the pharmaceutical composition, and relating to the vaccine delivery system are applicable to this aspect of the invention relating to the method of treating or preventing an infection or disease.

The administrative routes in these methods are the same as those described above for administrating the pharmaceutical composition and the vaccine delivery system.

The infection or disease to be treated may be a bacterial infection/disease, a viral infection/disease, a protozoan disease, a non-communicable disease, cancer, or an autoimmune disease. In some embodiments, the infection/disease is a viral infection/disease caused by an RNA virus. The RNA virus can be a hepatitis virus, a corona virus, a mosquito-borne virus (e.g., Venezuelan equine encephalitis (VEE) virus, or flavivirus such as ZIKV virus), or HIV. To prevent or treat these diseases, the bioactive agent in the nanoemulsion composition can be an antigen or a nucleic acid molecule encoding an antigen derived from a corona virus genome.

In certain embodiments, the RNA virus is a corona virus selected from the group consisting a MERS virus and a SARS virus. In one embodiment, the SARS virus is SARS-CoV-2.

In some embodiments, the method relates to treating or preventing a corona virus (such as SARS-CoV-2, "COVID-19") in a subject, and the method comprises:
administering to the subject a therapeutically effective amount of the nanoemulsion composition comprising the nanoemulsion particles and the bioactive agent, and optionally an adjuvant, wherein the bioactive agent is: an RNA that is an innate agonist, or an antigen or a nucleic acid molecule encoding an antigen derived from a corona virus genome (e.g., the SARS-CoV-2 genome).

In certain embodiments, the bioactive agent is an RNA that is an innate agonist. In one embodiment, the RNA is a RIG-I agonist, such as a PAMP. In one embodiment, the RNA is a TLR3 agonist, such as RIBOXXOL, poly(I:C), or Hiltonol®.

In certain embodiments, the bioactive agent is an RNA encoding an antigen derived from the corona virus genome (e.g., the SARS-CoV-2 genome). In one embodiment, the RNA is self-replicating. In one embodiment, the RNA encodes all or a portion of the spike "S" protein.

As discussed above, the inorganic solid nanoparticles, when containing a reporter element detectable via imaging methods, the resulting nanoemulsion particles can be imaged and tracked after the nanoemulsion particles are administered in the body. For instance, the inorganic solid nanoparticle may contain a reporter element detectable via magnetic resonance imaging (MRI), such as a paramagnetic, superparamagnetic, ferrimagnetic or ferromagnetic compound.

Accordingly, one aspect of the invention also relates to a method of imaging and/or tracking a bioactive agent delivery in a subject, comprising:
administering to the subject the nanoemulsion composition comprising the nanoemulsion particles and the bioactive agent, as described herein, wherein the inorganic nanoparticles contain materials detectable via magnetic resonance imaging, and
detecting the nanoemulsion composition with magnetic resonance imaging.

In one embodiment, the inorganic solid nanoparticle materials that are MRI-detectable are iron oxides, iron gluconates, and iron sulfates.

All above descriptions and all embodiments regarding the nanoemulsion composition, nanoemulsion particles (including liquid oil, inorganic nanoparticles, lipid such as cationic lipid, hydrophobic surfactant, and hydrophilic surfactant), bioactive agents, preparation of the nanoemulsion composition, pharmaceutical composition, and vaccine delivery system discussed above in the aspects of the invention relating to the nanoemulsion composition comprising the nanoemulsion particles, relating to the nanoemulsion composition comprising the nanoemulsion particles and a bioactive agent, relating to the method of making a nanoemulsion composition, relating to the pharmaceutical composition, and relating to the vaccine delivery system are applicable to this aspect of the invention relating to the method of imaging and/or tracking a bioactive agent delivery.

The imaging applications of the nanoemulsion compositions are very useful as they allow for real-time tracking the delivery of the bioactive agent by the nanoemulsion compositions (LION particles) in the subject. LIONs therefore not only can deliver the therapy, but also can self-report/tracking the disease and treatment through imaging.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In case of conflict, the present specification, including explanations of terms, will control. In addition, all the materials, methods, and examples are illustrative and not intended to be limiting.

EXAMPLES

The following examples are for illustrative purposes only and are not intended to limit, in any way, the scope of the present invention.

Example 1. General Production Techniques and Materials Employed in the Examples Materials The following materials were used in the manufacturing of lipid-inorganic nanoparticles (LIONs). Iron oxide nanoparticles at 25 mgFe/ml in chloroform and of various average diameters (5, 10, 15, 20, 25 and 30 nm) were purchased from Ocean Nanotech (San Diego, CA). Squalene and Span® 60 (sorbitan monostearate) were purchased from Millipore Sigma. Tween® 80 (polyethylene glycol sorbitan monooleate) and sodium citrate dihydrate were purchased from Fisher Chemical. The chloride salt of the cationic lipid 1,2-dioleoyl-3-trimethylammonium-propane (DOTAP chloride) was purchased from Corden Pharma. Ultrapure water (18.2 MOhm-cm resistivity) was obtained from a Milli-Q water purification system (Millipore Sigma).

Production of Lipid Inorganic Nanoparticles (LIONs) Labeled as 79-004.

These LIONs comprise 37.5 mg/ml squalene, 37 mg/ml Span® 60, 37 mg/ml Tween® 80, 30 mg/ml DOTAP chloride, 0.1 mg/ml 10 nm iron oxide nanoparticles and 10 mM sodium citrate dihydrate. The LIONs were manufactured using the following procedures.

In a 200 ml beaker, 0.4 ml of iron oxide nanoparticles at 25 mgFe/ml in chloroform, with a number-weighted average diameter of 10 nm, were added. Chloroform was allowed to evaporate in a fume hood leaving behind a dry coating of iron oxide nanoparticles. To the iron oxide nanoparticles, 3.7 grams of Span® 60, 3.75 grams of squalene, and 3 grams of DOTAP chloride were added to prepare the "oil" phase. The oil phase was sonicated 30 minutes in a water bath pre-heated to 60° C. Separately, in a 1 liter glass bottle, the "aqueous" phase was prepared by adding 39 grams of Tween® 80 to 1,000 ml 10 mM sodium citrate dihydrate solution prepared with Milli-Q water. The aqueous phase was stirred for 30 minutes to allow complete dissolution of Tween® 80. After complete dissolution of Tween® 80, 96 ml of the aqueous phase was transferred to a 200 ml beaker and incubated in a water bath pre-heated to 60° C. To the heated oil phase, 96 ml of the pre-heated aqueous phase was added. The mixture was immediately emulsified using a VWR® 200 homogenizer (VWR International) until a homogenous colloid with a milk-like appearance was produced. The colloid was subsequently processed by passaging the fluid through a Y-type interaction chamber of a LM10 microfluidizer at 20,000 psi. The fluid was passaged until the z-average hydrodynamic diameter, measured by dynamic light scattering (Malvern Zetasizer Nano S), was 54 nm with a 0.2 poly dispersity index. The microfluidized LION sample was terminally filtered with a 200 nm pore-size polyethersulfone (PES) syringe filter.

Production of Lipid Inorganic Nanoparticles (LIONs) Labeled as 79-006-A.

These LIONs comprise 37.5 mg/ml squalene, 37 mg/ml Span® 60, 37 mg/ml Tween® 80, 30 mg/ml DOTAP chloride, 0.2 mg/ml 15 nm iron oxide nanoparticles, and 10 mM sodium citrate dihydrate. The LIONs were manufactured using the following procedures.

In a 200 ml beaker, 0.8 ml of iron oxide nanoparticles at 25 mgFe/ml in chloroform, with a number-weighted average diameter of 15 nm, was added. Chloroform was allowed to evaporate in a fume hood leaving behind a dry coating of iron oxide nanoparticles. To the iron oxide nanoparticles, 3.7 grams of Span® 60, 3.75 grams of squalene, and 3 grams of DOTAP chloride were added to prepare the "oil" phase. The oil phase was sonicated 30 minutes in a water bath pre-heated to 60° C. Separately, in a 1 liter glass bottle, the "aqueous" phase was prepared by adding 39 grams of Tween® 80 to 1,000 ml of 10 mM sodium citrate dihydrate solution prepared with Milli-Q water. The aqueous phase was stirred for 30 minutes to allow complete dissolution of Tween® 80. After complete dissolution of Tween® 80, 96 ml of the aqueous phase was transferred to a 200 ml beaker and incubated in a water bath pre-heated to 60° C. To the heated oil phase, 96 ml of the pre-heated aqueous phase was added. The mixture was immediately emulsified using a VWR® 200 homogenizer (VWR International) until a homogenous colloid with a milk-like appearance was produced. The colloid was subsequently processed by passaging the fluid through a Y-type interaction chamber of a LM10 microfluidizer at 20,000 psi. The fluid was passaged until the z-average hydrodynamic diameter, measured by dynamic light scattering (Malvern Zetasizer Nano S), was 52 nm with a 0.2 poly dispersity index. The microfluidized LION sample was terminally filtered with a 200 nm pore-size polyethersulfone (PES) syringe filter.

Production of Lipid Inorganic Nanoparticles (LIONs) Labeled as 79-006-B.

These LIONs comprise 37.5 mg/ml squalene, 37 mg/ml Span® 60, 37 mg/ml Tween® 80, 30 mg/ml DOTAP chloride, 0.2 mg/ml 5 nm iron oxide nanoparticles, and 10 mM sodium citrate dihydrate. The LIONs were manufactured using the following procedures.

In a 200 ml beaker, 0.8 ml of iron oxide nanoparticles at 25 mgFe/ml in chloroform, with a number-weighted average diameter of 5 nm, was added. Chloroform was allowed to evaporate in a fume hood leaving behind a dry coating of iron oxide nanoparticles. To the iron oxide nanoparticles, 3.7 grams of Span® 60, 3.75 grams of squalene, and 3 grams of DOTAP chloride were added to prepare the "oil" phase. The oil phase was sonicated 30 minutes in a water bath pre-heated to 60° C. Separately, in a 1 liter glass bottle, the "aqueous" phase was prepared by adding 39 grams of Tween® 80 to 1,000 ml of 10 mM sodium citrate dihydrate solution prepared with Milli-Q water. The aqueous phase was stirred for 30 minutes to allow complete dissolution of Tween® 80. After complete dissolution of Tween® 80, 96 ml of the aqueous phase was transferred to a 200 ml beaker and incubated in a water bath pre-heated to 60° C. To the heated oil phase, 96 ml of the pre-heated aqueous phase was added. The mixture was immediately emulsified using a VWR® 200 homogenizer (VWR International) until a homogenous colloid with a milk-like appearance was produced. The colloid was subsequently processed by passaging the fluid through a Y-type interaction chamber of a LM10 microfluidizer at 20,000 psi. The fluid was passaged until the z-average hydrodynamic diameter, measured by dynamic light scattering (Malvern Zetasizer Nano S), was 59 nm with a 0.2 poly dispersity index. The microfluidized LION sample was terminally filtered with a 200 nm pore-size polyethersulfone (PES) syringe filter.

Production of Lipid Inorganic Nanoparticles (LIONs) Labeled as 79-011.

These LIONs comprise 9.4 mg/ml squalene, 9.3 mg/ml Span® 60, 9.3 mg/ml Tween® 80, 7.5 mg/ml DOTAP chloride, 0.05 mg/ml 25 nm iron oxide nanoparticles, and 10 mM sodium citrate dihydrate. The LIONs were manufactured using the following procedures.

In a 200 ml beaker, 0.2 ml of iron oxide nanoparticles at 25 mgFe/ml in chloroform, with a number-weighted average diameter of 25 nm, was added. Chloroform was allowed to evaporate in a fume hood leaving behind a dry coating of iron oxide nanoparticles. To the iron oxide nanoparticles, 0.93 grams of Span® 60, 0.94 grams of squalene, and 0.75 grams of DOTAP chloride were added to prepare the "oil" phase. The oil phase was sonicated 30 minutes in a water bath pre-heated to 60° C. Separately, in a 1 liter glass bottle, the "aqueous" phase was prepared by adding 10 grams of Tween® 80 to 1,000 ml of 10 mM sodium citrate dihydrate solution prepared with Milli-Q water. The aqueous phase was stirred for 30 minutes to allow complete dissolution of Tween® 80. After complete dissolution of Tween® 80, 99 ml of the aqueous phase was transferred to a 200 ml beaker and incubated in a water bath pre-heated to 60° C. To the heated oil phase, 96 ml of the pre-heated aqueous phase was added. The mixture was immediately emulsified using a VWR® 200 homogenizer (VWR International) until a homogenous colloid with a milk-like appearance was produced. The colloid was subsequently processed by passaging the fluid through a Y-type interaction chamber of a LM10 microfluidizer at 20,000 psi. The fluid was passaged until the z-average hydrodynamic diameter, measured by dynamic light scattering (Malvern Zetasizer Nano S), was 60 nm with a 0.2 polydispersity index. The microfluidized LION sample was terminally filtered with a 200 nm pore-size polyethersulfone (PES) syringe filter.

Production of Lipid Inorganic Nanoparticles (LIONs) Labeled as 79-014-A.

These LIONs comprise 9.4 mg/ml squalene, 0.63 mg/ml Dynasan® 114 (trimyristin), 9.3 mg/ml Span® 60, 9.3 mg/ml Tween® 80, 7.5 mg/ml DOTAP chloride, 0.05 mg/ml 15 nm iron oxide nanoparticles, and 10 mM sodium citrate dihydrate. The LIONs were manufactured using the following procedures.

In a 200 ml beaker, 0.2 ml of iron oxide nanoparticles at 25 mgFe/ml in chloroform, with a number-weighted average diameter of 15 nm, was added. Chloroform was allowed to evaporate in a fume hood leaving behind a dry coating of iron oxide nanoparticles. To the iron oxide nanoparticles, 0.93 grams of Span® 60, 0.94 grams of squalene, 0.063 grams Dynasan® 114, and 0.75 grams of DOTAP chloride were added to prepare the "oil" phase. The oil phase was sonicated 30 minutes in a water bath pre-heated to 60° C. Separately, in a 1 liter glass bottle, the "aqueous" phase was prepared by adding 10 grams of Tween® 80 to 1,000 ml of 10 mM sodium citrate dihydrate solution prepared with Milli-Q water. The aqueous phase was stirred for 30 minutes to allow complete dissolution of Tween® 80. After complete dissolution of Tween® 80, 99 ml of the aqueous phase was transferred to a 200 ml beaker and incubated in a water bath pre-heated to 60° C. To the heated oil phase, 96 ml of the pre-heated aqueous phase was added. The mixture was immediately emulsified using a VWR® 200 homogenizer (VWR International) until a homogenous colloid with a milk-like appearance was produced. The colloid was subsequently processed by passaging the fluid through a Y-type interaction chamber of a LM10 microfluidizer at 20,000 psi. The fluid was passaged until the z-average hydrodynamic diameter, measured by dynamic light scattering (Malvern Zetasizer Nano S), was 60 nm with a 0.2 polydispersity index. The microfluidized LION sample was terminally filtered with a 200 nm pore-size polyethersulfone (PES) syringe filter.

Example 2. Stability of the LION Formulations

LION Formulations are Thermostable.

Figure 1B:
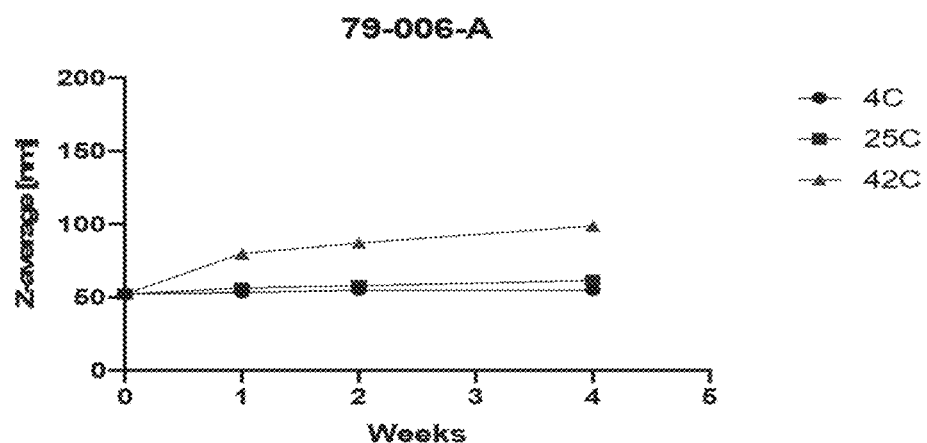
Figure 1C:
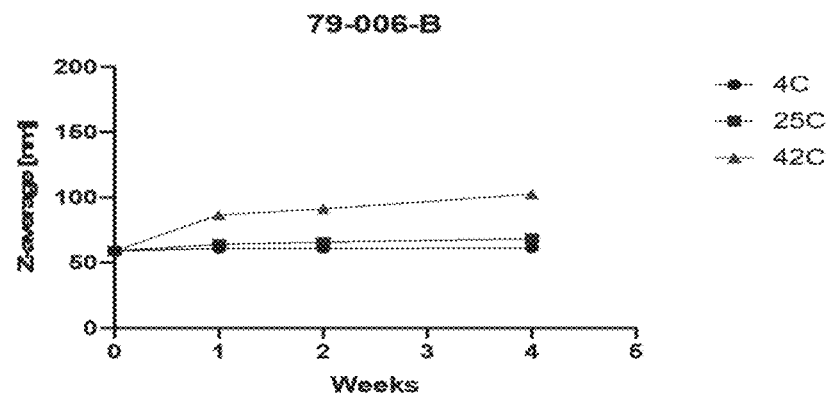

Various formulations (LIONs labeled as 79-004, 79-006-A, and 79-006-B, respectively, as prepared in Example 1) were placed into a stability chamber at the indicated temperatures. The stability was determined by particle size measurement using dynamic light scattering. The results show that the LION formulation formed a stable colloid when stored at 4, 25 and 42° C. As demonstrated in FIGS. 1A-1C, the particles in the LION formulations show exceptional stability over a range of temperature and over time.

LION Formulations Protect RNA from RNases.

This example shows that LION formulations protect RNAs from ribonuclease (RNase)-catalyzed degradation. The protection from RNase challenge was characterized by gel electrophoresis. RNA molecules were complexed with the LION formulations by mixing at a predetermined nitrogen:phosphate (N:P) ratio. Various LION formulations were bound to RNA and the complexes were exposed to RNase.

One hundred μl of naked (unformulated) RNA or RNA complexed with LION formulations (LIONs labeled as 79-004, 79-006-A, 79-006-B, and 79-011, respectively, as prepared in Example 1) at N:P of 15 was incubated at room temperature for 30 minutes with RNase A solution (Thermo Scientific, EN053L) diluted to 10 mg/L. After 30 minutes, proteinase K solution (Thermo Scientific, EO0491) diluted to 1 mg/ml was added and all samples were heated to 55° C. for 10 minutes. To extract RNA, 0.12 ml phenol:chloroform solution (Invitrogen, 15593-031) was added to all samples; samples were vortexed for 15 seconds and centrifuged at 13,300 rpm for 15 minutes. 20 μl of supernatant was extracted and transferred to a PCR tube, and 20 μl of glyoxal load dye (Invitrogen, AM8551) was added to each tube. All samples were heated at 50° C. for 20 minutes. Samples containing 250 ng of RNA were loaded in the wells of a 1% agarose gel immersed in a Northern Max Gly Gel Prep running buffer (Ambion, AM8678) in a gel electrophoresis box. Gel was run at 120 V for 45 minutes and imaged in a gel documentation system. The results are shown in FIG. 2.

Figure 2:
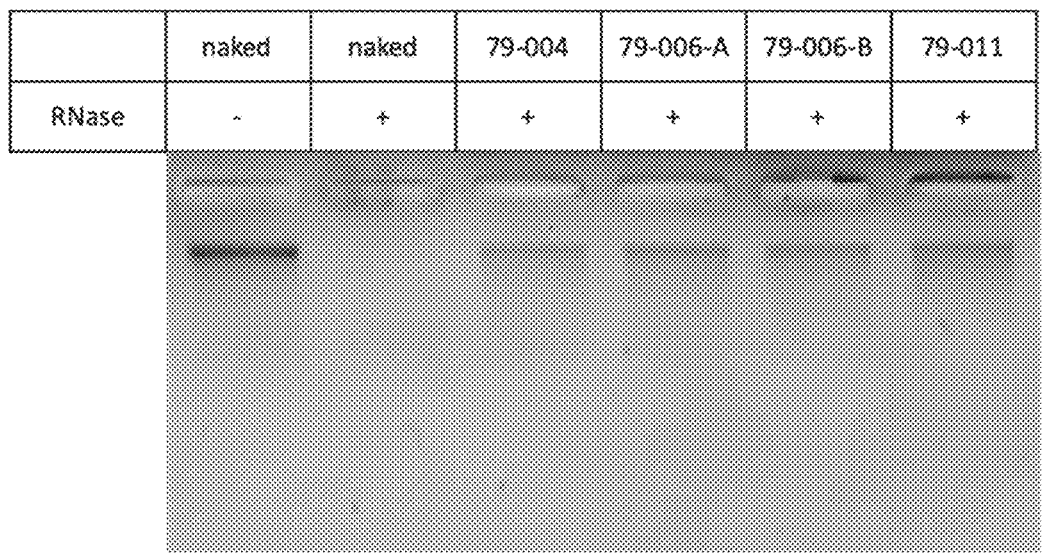
FIG. 2 shows the gel electrophoresis of exemplary LION formulations (LIONs labeled as 79-004, 79-006-A, 79-006-B, and 79-011, respectively, as prepared in Example 1) complexed with RNA molecules at nitrogen:phosphate (N:P) ratio of 15, as compared to the naked (unformulated) RNA, demonstrating the ability of the LION formulations to protect RNA from the action of RNases.

FIG. 2 shows the gel electrophoresis of exemplary LION formulations (LIONs labeled as 79-004, 79-006-A, 79-006-B, and 79-011, respectively, as prepared in Example 1) complexed with RNA molecules at nitrogen:phosphate (N:P) ratio of 15, as compared to the naked (unformulated) RNA. FIG. 2 demonstrates the stability of RNA protected by the LION formulation to the action of RNase. As shown in FIG. 2, the naked RNA (without complexing with a LION formulation) treated with RNase was completely destroyed, while all the LION formulations protected the RNA being complexed with.

Example 3. Using LION Formulations for Protein Expression—Secreted Embryonic Alkaline Phosphatase "SEAP" Expression This example demonstrates that the LION formulations drive high levels of Secreted Embryonic Alkaline Phosphatase (SEAP) expression. Messenger RNA molecules encoding a protein of interest were complexed with a LION formulation, which was delivered in the cytoplasm of cells of an organism. The messenger RNA underwent intracellular translation and produced the protein of interest. The subgenome of the attenuated replicating alphavirus Venezuelan equine encephalitis (VEE) virus, TC-83, was modified by substituting secreted embryonic alkaline phosphatase (SEAP) for VEE structural proteins.

One μg of the modified replicon RNA encoding SEAP (RNA-SEAP) was complexed with LION formulation labeled as 79-004 (10 nm, Example 1) at N:P of 15 and administered intramuscularly (50 μl) in C57BL/6 mice (n=3). Mice were bled at regular intervals, and protein expression was determined by assaying mouse sera for SEAP on days −1 (pre-injection), 3, 5, 7, 9, 11, 13, 15 and 20. The results of SEAP expression in mouse over days post injection are shown in FIG. 3A.

Figure 3A:
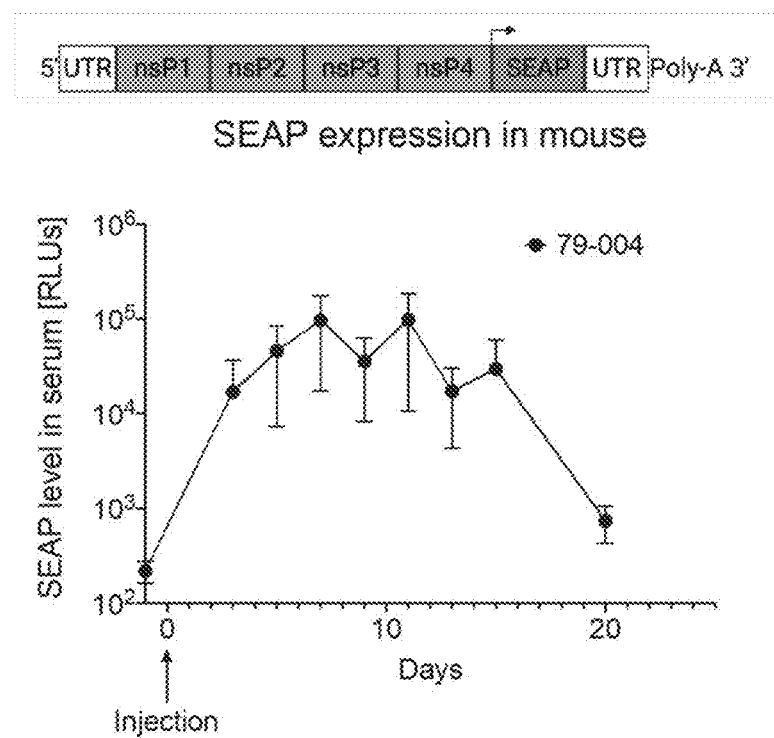
FIG. 3A shows the protein expression in C57BL/6 mice injected intramuscularly with repRNA-encoding SEAP formulated with an LION formulation (LION labeled as 79-004, as prepared in Example 1) over a prolonged period of time.

FIG. 3A shows that LION formulations complexed with messenger RNAs can express robust levels of secreted protein over a prolonged stretch of time (20 days after injection).

Impact of the Size of the Core Inorganic Particles

Figure 3B:
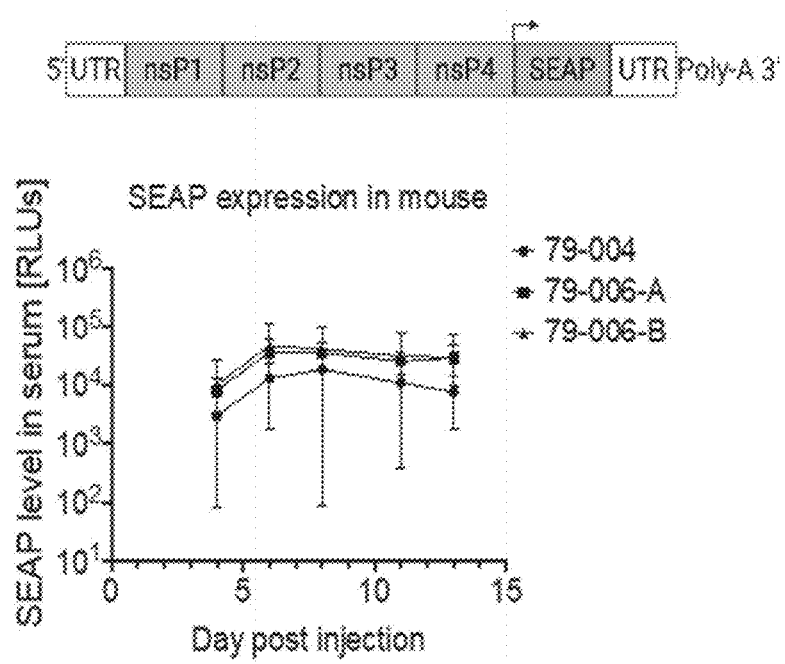
FIG. 3B shows the protein expression in C57BL/6 mice injected intramuscularly with repRNA-encoding SEAP formulated with various LION formulations varying SPIO sizes (LIONs labeled as 79-004, 79-006-A, and 79-006-B, respectively, as prepared in Example 1) over days post injection.

RepRNA encoding-SEAP (1 μg) was complexed with LION formulation labeled as 79-004, 79-006-A, or 79-006-B (with varying SPIO sizes, see Example 1) at a N:P ratio of 15 and administered intramuscularly (50 μl) in C57BL/6 mice (n=3/formulation). Mice were bled at regular intervals, and protein expression was determined by assaying mouse sera for SEAP on days 4, 6, 8, 11, 13, 15 and 20. The results of SEAP expression in mouse over days post injection are shown in FIG. 3B. Log-transformed data was analyzed by two-way ANOVA and Tukey's multiple comparisons test.

FIG. 3B shows that LION formulations with the core inorganic SPIO nanoparticles having varying average diameters all worked to induce similar robust levels of protein expression in vivo over a prolonged time period, with no statistically significant difference in SEAP expression between there formulations. Thus, the diameter of SPIO particles did not appear to impact the ability of the LION formulation to deliver repRNA molecules and the level of protein expression from the repRNA molecules.

LION Delivery Vs. NLC Delivery

The modified repRNA-encoding SEAP (RNA-SEAP) (1 μg) was complexed with LION formulation labeled as 79-004 (10 nm, Example 1) at N:P of 15, or with a nanostructured lipid carrier (NLC) as control. The resulting RNA-LION formulation was administered intramuscularly (50 μl) in C57BL/6 mice (n=3). Mice were bled at regular intervals, and protein expression was determined by assaying mouse sera for SEAP. The results of SEAP expression in mouse over days post injection are shown in FIG. 3C.

The control is nanostructured lipid carrier (NLC) which is a blend of solid lipid (glyceryl trimyristate-dynasan) and liquid oil (squalene) that forms a semi-crystalline core upon emulsification. See more detailed description about the NLC in Erasmus et al., "A Nanostructured Lipid Carrier for Delivery of a Replicating Viral RNA Provides Single, Low-Dose Protection against Zika," Mol. Ther. 26(10):2507-22 (2018), which is incorporated herein by reference in its entirety.

Figure 3C:
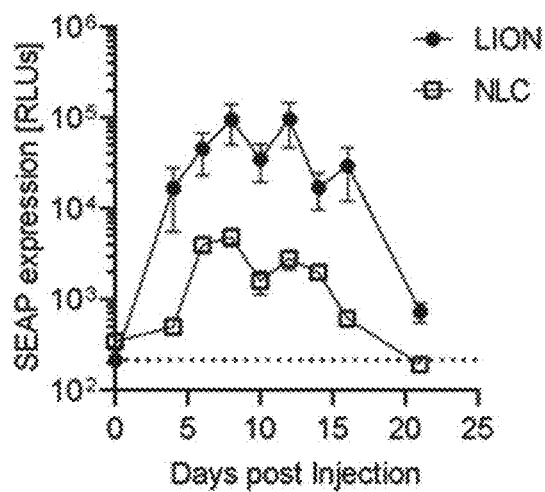
FIG. 3C shows the protein expression in C57BL/6 mice injected intramuscularly with repRNA-encoding SEAP formulated with an LION formulation, or with a nanostructured lipid carrier (NLC) as control, over days post injection.

As shown in FIG. 3C, the repRNA-encoding SEAP complexed with LION formulations resulted in higher overall levels of SEAP expression at each time point, as compared to the repRNA-encoding SEAP complexed with NLC. This indicates that compared to NLC, LION formulation served as a better delivery vehicle for repRNA molecules. Also, as shown in FIG. 3C, SEAP expression peaked around day 8, and by day 21, it returned to baseline for the control NLC group and to 0.5 log of baseline for the LION group.

Impact of the RNA Complexing Concentrations

RepRNA encoding-SEAP was complexed with LION formulation (15 nm, similar to 79-006A in Example 1) at a N:P ratio of 15, with varying the complexing concentration. The resulting RNA-LION formulations were administered intramuscularly in C57BL/6 mice (n=5/formulation). Mice were bled at regular intervals after intramuscular injection, and protein expression was determined by assaying mouse sera. The results of SEAP expression in mouse over days post injection are shown in FIG. 3D.

The RNA complexing concentration affected the size of the LION/repRNA complex. The LION/repRNA complex having a 10-fold higher repRNA concentration (400 ng/µl vs. 40 ng/µl) resulted in about 41% larger LION/repRNA-SEAP complex and 24% wider size distribution.

Figure 3D:
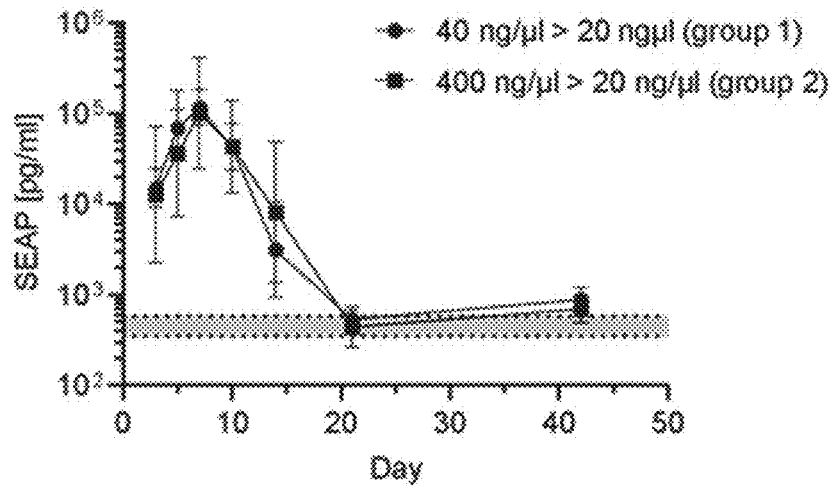
FIG. 3D shows the protein expression in C57BL/6 mice injected intramuscularly with repRNA-encoding SEAP formulated with an LION formulation at a RNA complex concentration of 400 ng/µl and 40 ng/µl, respectively, over days post injection.

As shown in FIG. 3D, there was no significant difference in the mean SEAP concentration at each time point (using Mann-Whitney test) for the LION/repRNA complexes having concentrations of 400 ng/µl vs. 40 ng/µl, suggesting that the complexing concentration did not have a substantial effect on the repRNA delivery and protein expression. For either repRNA concentration (400 ng/µl vs. 40 ng/µl), the SEAP expression concentration in the serum of mice immunized with the LION/repRNA-SEAP formulation peaked on Day 7 post intramuscular injection, and returned to background levels by Day 21.

Impact of the N:P and RNA Dose

RepRNA encoding-SEAP (at 0.5 µg, 2.5 µg, and 12.5 µg, respectively) was complexed with LION formulation (15 nm, similar to 79-006A in Example 1) with varying the N:P ratio. The resulting RNA-LION formulations were administered intramuscularly in C57BL/6 mice (n=4/formulation). Mice were bled 7 days after intramuscular injection, and protein expression was determined by assaying mouse sera. The results of SEAP expression in mouse as a function of N:P ratio are shown in FIG. 3E.

Figure 3E:
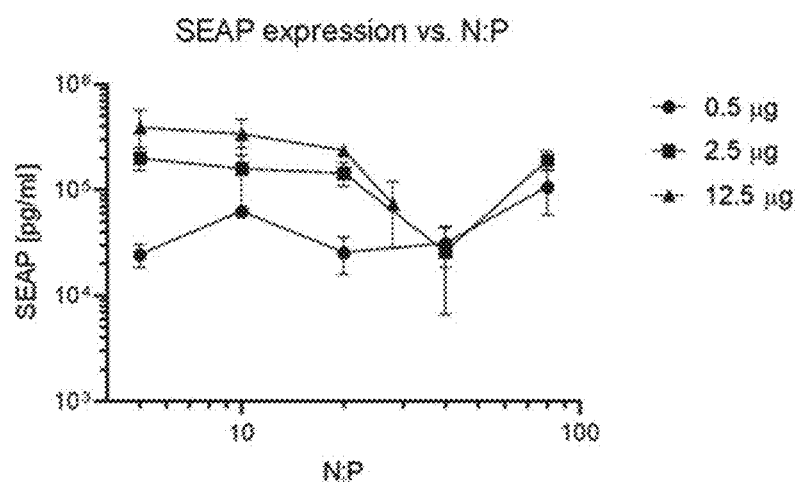
FIG. 3E shows the protein expression in C57BL/6 mice injected intramuscularly with repRNA-encoding SEAP (at 0.5 µg, 2.5 µg, and 12.5 µg, respectively) formulated with an LION formulation as a function of the N:P ratio. Data are displayed as mean and SE.

FIG. 3E shows the impact of N:P ratio and RNA dose on the bioactivity of LION formulated repRNA.

Example 4. Using LION Formulations for Vaccine Delivery

This example shows that antigens expressed off of LION-complexed RNA are highly immunogenic and induce antibodies. RNA molecules encoding a vaccine antigen were complexed with a LION formulation, which were delivered in the cytoplasm of cells of an organism. The RNA underwent intracellular translation and produced the vaccine antigen. The organism mounted an immune response by producing antibodies against the antigen.

Figure 4A:
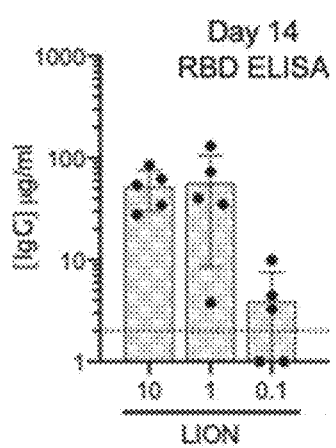
FIG. 4A shows that the antigens expressed from the LION/repRNA complex (at the dosage levels of 10, 1, and 0.1 µg of srRNA) induced immune response to the receptor-binding domain of SARS-CoV-2 in C57BL/6 mice.
Figure 4B:
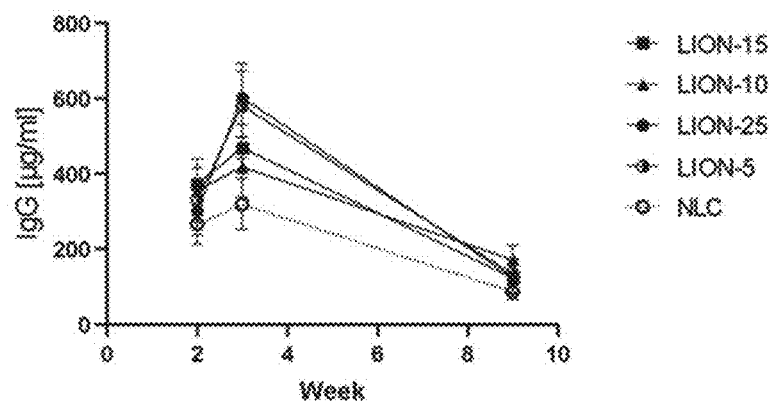
FIG. 4B shows the results of anti-S IgG concentrations in the serum of the C57BL/6 mice injected intramuscularly with repSARS-CoV2S formulated with various LION formulations varying SPIO size (LION-10, LION-15, LION-25, LION-5 respectively), determined by anti-Spike enzyme linked immunosorbent assay (ELISA). Data are displayed as mean and SE; n=5 per group.
Figure 4C:
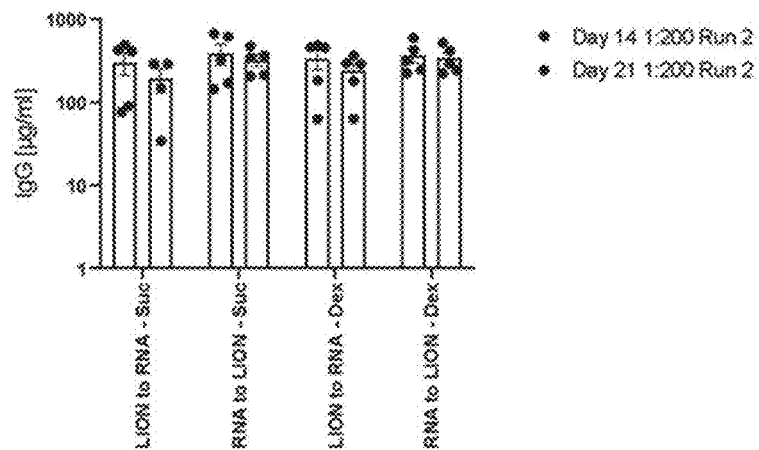
FIG. 4C shows the results of anti-S IgG concentrations in the serum of the C57BL/6 mice injected intramuscularly with repSARS-CoV2S formulated with various LION formulations by varying the mixing direction (mixing LION to RNA vs. mixing RNA to LION) and diluent (1:200 dilution using sucrose (Suc) vs. using dextrose (Dex)), at Day 14 (first bar for each group) or Day 21 (second bar for each group) after intramuscular injection, determined by anti-Spike ELISA. Data are displayed as mean and SE; n=5 per group.

A self-replicating "sr" RNA preparation, encoding a form of the spike "S" protein full-length, was mixed and formulated with LIONs. Mice were immunized once intramuscularly, with the formulated test articles at the dosage levels of 10, 1, and 0.1 µg of srRNA. At 14 days post-immunization, animals were bled, sera prepared and stored in aliquots at −20° C. until use. Antigen-specific IgG concentration using a polyclonal IgG standard were determined against a truncated receptor-binding domain (RBD) protein fragment. The results are shown in FIG. 4A. As seen in FIG. 4A, the antigens expressed off of the LION/repRNA formulations at various doses of RNA (10, 1, and 0.1 µg, respectively) all induced strong and robust immune responses to the receptor binding domain of SARS-CoV-2. Robust titers were seen even at very low concentrations of RNA (0.1 µg).

Figure 5A:
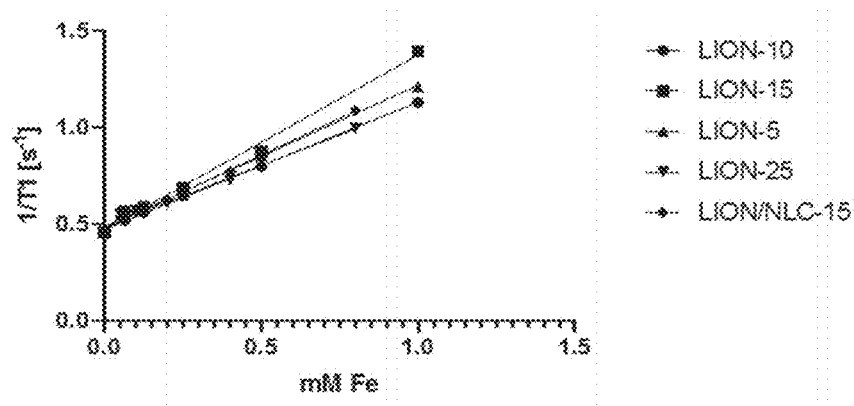
FIGS. 5A-5B show the enhancement in T1 (FIG. 5A) and T2 (FIG. 5B) relaxation times as a function of iron concentration in LION formulations.
Figure 5B:
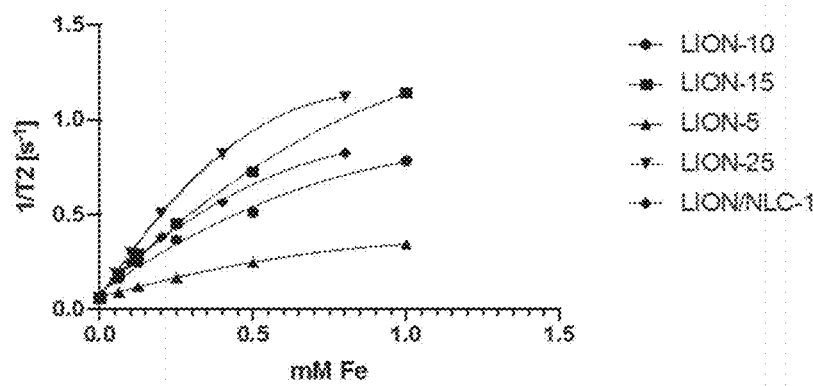

Impact of the Size of the Core Inorganic Particles; LION Delivery Vs. NLC Delivery RepSARS-CoV2S RNAs complexed with various LION formulations varying SPIO size (LION-10, LION-15, LION-25, LION-5 respectively), or with a nanostructured lipid carrier (NLC) as control, were administered intramuscularly in C57BL/6 mice. The formulations labeled as LION-10, LION-15, LION-25, and LION-5 correspond to the LION compositions labeled as 79-004, 79-006-A, 79-006-B, 79-011, 79-014-A, respectively (see Table 1 below; see also Example 1). Mice were bled at regular intervals after intramuscular injection, and protein expression was determined by assaying IgG concentrations by anti-Spike (anti-S) enzyme linked immunosorbent assay (ELISA). The results of anti-S IgG concentrations in the serum of the C57BL/6 mice over weeks post injection are shown in FIG. 4B.

FIG. 4B shows that LION formulations with the core inorganic SPIO nanoparticles having varying average diameters all worked to retain the biological activity of antigens and induced robust levels of immune response in vivo over a prolonged time period. Moreover, all RepSARS-CoV2S RNAs that were complexed with the LION formulations generated responses greater than those complexed with the control NLC.

Impact of Mixing Direction and Dilution

RepSARS-CoV2S RNAs complexed with various LION formulations, prepared by varying the mixing direction (mixing LION to RNA vs. mixing RNA to LION) and diluent (1:200 dilution using sucrose (Suc) vs. using dextrose (Dex)), were administered intramuscularly in C57BL/6 mice. Mice were bled at Day 14 (first bar for each group) or Day 21 (second bar for each group) after intramuscular injection, and protein expression was determined by assaying IgG concentrations by anti-Spike ELISA. The results are shown in FIG. 4C.

As shown in FIG. 4C, the direction of mixing (whether mixing LION to RNA or mixing RNA to LION) did not impact the biological activity of antigens and the ability of the LION formulations to deliver the RNAs. Moreover, varying diluents (dextrose or sucrose) of the LION-RNA formulations did not impact the biological activity of antigens.

Example 5. Imaging LION Formulations

This example shows that LION formulations can emit signals for an MRI imaging. LION formulations complexed to RNA molecules or conjugated with molecules to the nanoparticle surface or with molecules encapsulated in the lipid core were administered to an organism. The organism was subsequently placed in an imaging instrument and exposed to electromagnetic waves, and the LION nanoparticles served to enhance the contrast. The results are shown in FIGS. 5A-5B.

FIGS. 5A-5B show the enhancement in T1 (FIG. 5A) and T2 (FIG. 5B) relaxation times as a function of iron concentration in LION formulations. The compositions of the LION formulations identified in FIGS. 5A-5B correspond to each of the LION compositions labeled as 79-004, 79-006-A, 79-006-B, 79-011, 79-014-A, respectively (see Table 1 below), according to Example 1, except that the concentrations of iron oxides in the LION composition were varies based on the X axis in the figures.

FIG. 5 summarizes the ability to enhance both T1 and T2 contrast in magnetic resonance imaging (MRI) using LION particles 79-004, 79-006-A, 79-006-B, 79-011 and 79-014-A. The r1, r2 relaxivities and r2/r1 ratios are summarized in Table 1.

TABLE 1

MR relaxivity (r1 and r2) and r2/r1 ratios of LION formulations containing iron oxides core with various core diameters.

| | Formulation | | | | |
|---|---|---|---|---|---|
| | 79-004 | 79-006-A | 79-006-B | 79-011 | 79-014-A |
| Alt. name | LION-10 | LION-15 | LION-5 | LION-25 | LION/NLC-15 |
| r1 [mM−1 s−1] | 0.66 | 0.91 | 0.74 | 0.63 | 0.76 |
| r2 [mM−1 s−1] | 1.12 | 1.59 | 0.46 | 2.47 | 1.60 |
| r2/r1 | 1.70 | 1.75 | 0.63 | 3.94 | 2.10 |

Example 6. Using LION Formulations for Antibody Expression

This example shows that antibodies can be launched off of LION-complex RNA. RNA molecules encoding an antibody was complexed with a LION formulation and delivered in the cytoplasm of cells of an organism. The messenger RNA underwent intracellular translation and produced the antibody.

Figure 6A:
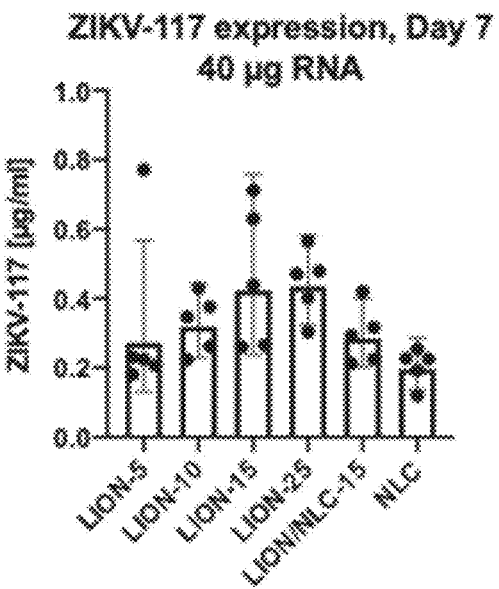
FIG. 6A shows the LION-antibody sequence RNA complex induced ZIKV-117 antibodies in animals. Animals were bled 7 days after immunization.

LION Formulation with a Replicon RNA Encoding a Monoclonal Antibody Targeting Zika Virus FIG. 6A shows robust levels of a human monoclonal antibody (ZIKV-117) that recognizes the Zika virus being produced after immunization of animals with the LION/antibody sequence RNA (at 40 µg RNA) formulation, varying SPIO size of the LION formulation (LION-10, LION-15, LION-25, LION-5 respectively). Animals were bled 7 days after immunization. The results indicate that LION formulations can be used to produce antibodies in a living organism. A nanostructured lipid carrier (NLC) formulated with the antibody sequence RNA was used as control. As shown in FIG. 6A, the antibody sequence RNA complexed with LION formulations resulted in higher overall levels of ZIKV-117 expression with each SIPO size, as compared to the antibody sequence RNA complexed with NLC. This indicates that compared to NLC, LION formulation served as a better delivery vehicle for antibody sequence RNAs.

Figure 6B:
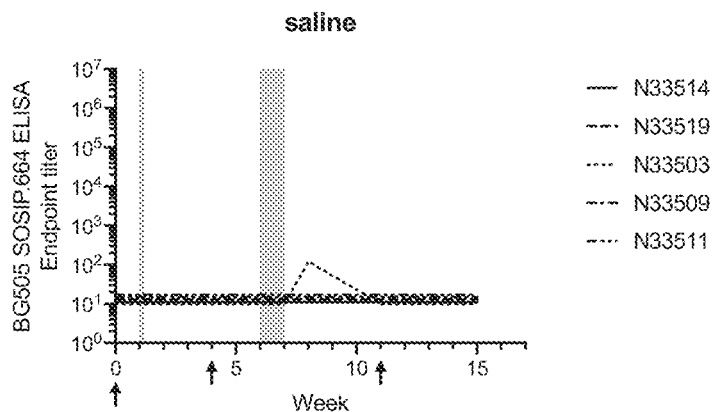
FIGS. 6B and 6C show the magnitude and kinetics of anti-BG505 SOSIP.664 IgG antibodies in adult female pregnant rabbits immunized by intramuscular route with saline (FIG. 6B) or repRNA encoding BG505 SOSIP.664 trimer formulated with LION (FIG. 6C).
Figure 6C:
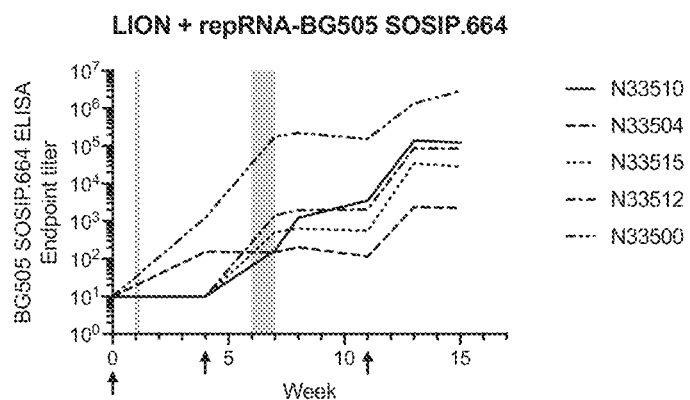
Figure 6D:
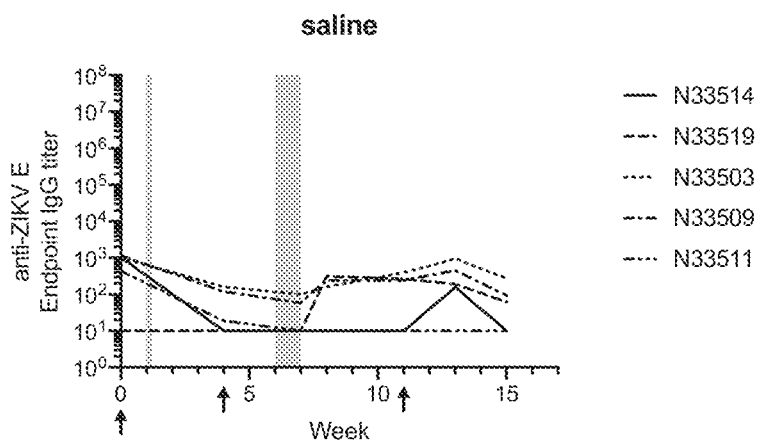
FIGS. 6D and 6E show the magnitude and kinetics of anti-ZIKV E IgG antibodies in adult female pregnant rabbits immunized by intramuscular route with saline (FIG. 6D) or repRNA encoding ZIKV prM-E antigens formulated with LION (FIG. 6E). The shaded region around week 1 marks the period when rabbits were bred. The shaded region between weeks 6 and 7 marks the period when kits were delivered. Arrows mark immunization time points (weeks 0, 4 and 11).
Figure 6E:
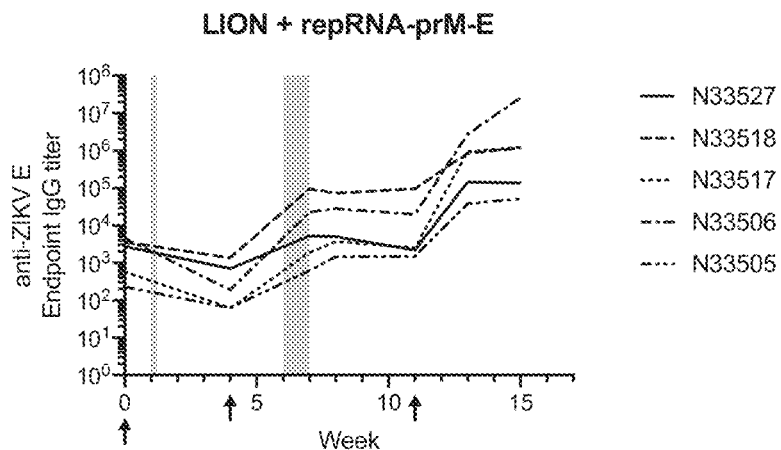

LION Formulation with HIV and ZIKV Vaccine Candidates for Maternal Immunization in a Rabbit Model FIGS. 6B and 6C show the magnitude and kinetics of anti-BG505 SOSIP.664 IgG antibodies in adult female pregnant rabbits immunized by intramuscular route with saline (FIG. 6B) or repRNA encoding BG505 SOSIP.664 trimer formulated with LION (FIG. 6C). FIGS. 6D and 6E show the magnitude and kinetics of anti-ZIKV E IgG antibodies in adult female pregnant rabbits immunized by intramuscular route with saline (FIG. 6D) or repRNA encoding ZIKV prM-E antigens formulated with LION (FIG. 6E). The shaded region around week 1 marks the period when rabbits were bred. The shaded region between weeks 6 and 7 marks the period when kits were delivered. Arrows mark immunization time points (weeks 0, 4 and 11). The results show that the antigens expressed off of the LION/repRNA formulations induced strong and robust immune responses and produced strong levels of antibodies for both LION/repRNA formulations.

Figure 6F:
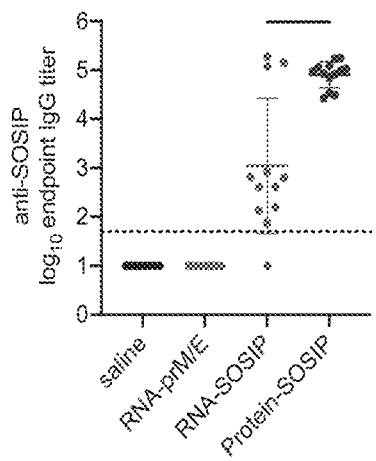
FIGS. 6F and 6G show the results for the evaluation of in utero transfer of anti-SOSIP IgG from rabbit does to rabbit kits.
Figure 6G:
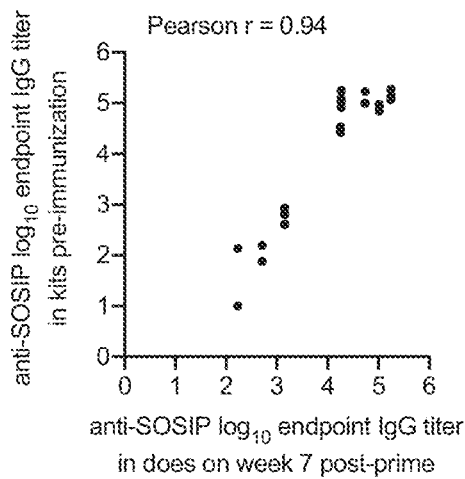

FIGS. 6F and 6G show the results for the evaluation of in utero transfer of anti-SOSIP IgG from rabbit does (female rabbits) to rabbit kits (rabbit babies). FIG. 6F shows anti-SOSIP IgG responses in rabbit kits at time of delivery. A minimum of two rabbit kits from each litter per treatment group were euthanized to evaluate in utero antibody transfer. FIG. 6G shows the XY plot demonstrating a positive correlation (Pearson r=0.94) between antibody levels in rabbit does and corresponding rabbit kits. These figures demonstrated the material transfer of antibody from the breeding rabbit does to rabbit kits.

Figure 6H:
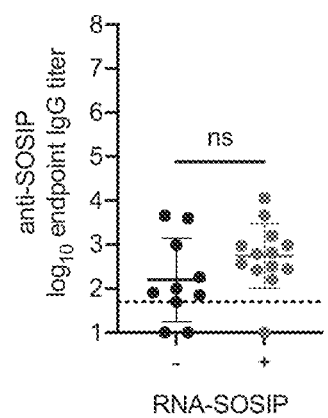
FIGS. 6H and 6I show the vaccine-induced responses in the context of pre-existing maternal antibodies. Serum anti-SOSIP IgG levels were collected in rabbit kits 4 weeks post-boost (3 weeks after kits were weaned). The rabbit kits from rabbit does receiving saline or from rabbit does receiving LION+RNA-prM/E are grouped as negative (−) for pre-existing maternal antibodies against BG505 SOSIP.664. The rabbit kits from rabbit does receiving LION+RNA-SOSIP or AddaVax adjuvanted recombinant BG505 SOSIP.664 are grouped as positive (+) for pre-existing maternal antibodies against BG505 SOSIP.664. Ordinary one-way ANOVA and Tukey's multiple comparisons test was performed on log 10 transformed data. (ns=non significant).
Figure 6I:
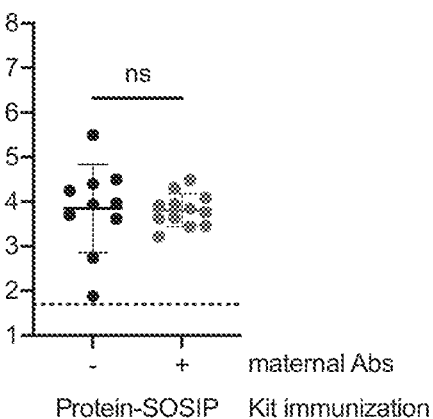

FIGS. 6H and 6I show the vaccine-induced responses in the context of pre-existing maternal antibodies. Serum anti-SOSIP IgG levels were collected in rabbit kits 4 weeks post-boost (3 weeks after kits were weaned). The rabbit kits from rabbit does receiving saline or from rabbit does receiving LION+RNA-prM/E are grouped as negative (−) for pre-existing maternal antibodies against BG505 SOSIP.664. The rabbit kits from rabbit does receiving LION+RNA-SOSIP or AddaVax adjuvanted recombinant BG505 SOSIP.664 are grouped as positive (+) for pre-existing maternal antibodies against BG505 SOSIP.664. Data show that pre-existing antibodies did not have a significant impact on vaccine-mediated induction of antibodies, and that passively transferred antibodies in rabbit kits did not negatively impact on vaccine-mediated induction of antibodies in rabbit kits.

Example 7. Using LION Formulations for Vaccine Delivery in Nonhuman Primates-Single-Dose Replicating RNA Vaccine Induces Neutralizing Antibodies Against SARS-CoV-2 in Nonhuman Primates This example discusses the development of repRNA-CoV2S, a stable and highly immunogenic vaccine candidate comprising an RNA replicon formulated with a novel Lipid InOrganic Nanoparticle (LION) designed to enhance vaccine stability, delivery and immunogenicity.

Vaccine Design, Preparation, and Characterization

Coronavirus Disease 2019 (COVID-19), caused by severe acute respiratory syndrome coronavirus-2 (SARS-CoV-2) infection, has been declared a worldwide pandemic. Coronaviruses are enveloped, single-strand positive-sense RNA viruses with a large genome and open reading frames for four major structural proteins: Spike (S), envelope, membrane, and nucleocapsid. The S protein mediates binding of coronaviruses to angiotensin converting enzyme 2 (ACE2) on the surface of various cell types including epithelial cells of the pulmonary alveolus. Protection may be mediated by neutralizing antibodies against the S protein, as most of the experimental vaccines developed against the related SARS-CoV incorporated the S protein, or its receptor binding domain (RBD), with the goal of inducing robust, neutralizing responses. Previous reports have shown that human-neutralizing antibodies protected mice, challenged with SARS-CoV and Middle East respiratory syndrome (MERS)-CoV, suggesting that protection against SARS-CoV-2 may be mediated through anti-S antibodies. Additionally, SARS vaccines that drive Type 2 T helper (Th2) responses have been associated with enhanced lung immunopathology following challenge with SARS-CoV, while those with a Type 1 T helper (Th1)-biased immune response have been associated with enhanced protection in the absence of immunopathology. An effective COVID-19 vaccine, therefore, may need to induce Th1-biased immune responses comprising SARS-CoV-2-specific neutralizing antibodies.

Nucleic acid vaccines have emerged as ideal modalities for rapid vaccine design, requiring only the target antigen's gene sequence and removing dependence on pathogen culture (inactivated or live attenuated vaccines) or scaled recombinant protein production. In addition, nucleic acid vaccines can avoid pre-existing immunity that can dampen immunogenicity of viral vectored vaccines. Clinical trials have been initiated with messenger RNA (mRNA) vaccines formulated with lipid nanoparticles (LNPs) and a DNA vaccine delivered by electroporation. However, mRNA and DNA vaccines may not be able to induce protective efficacy in humans after a single immunization, because, similar to inactivated and recombinant subunit protein vaccines, they typically require multiple administrations over an extended period of time to become effective.

Virus-derived replicon RNA (repRNA) vaccines were first described in 1989 and have been delivered in the forms of virus-like RNA particles (VRP), in-vitro transcribed (IVT) RNA, and plasmid DNA. In repRNA, the open reading frame encoding the viral RNA polymerase complex (most commonly from the Alphavirus genus) is intact but the structural protein genes are replaced with an antigen-encoding gene. While conventional mRNA vaccines are translated directly from the incoming RNA molecules, introduction of repRNA into cells initiates ongoing biosynthesis of antigen-encoding RNA that results in dramatically increased expression and duration that significantly enhances humoral and cellular immune responses. In addition, repRNA vaccines mimic an alphavirus infection in that viral-sensing stress factors are triggered and innate pathways are activated through Toll-like receptors and retinoic acid inducible gene (RIG)-I to produce interferons, pro-inflammatory factors and chemotaxis of antigen-presenting cells, as well as promoting antigen cross-priming. As a result, repRNA acts as its own adjuvant, eliciting more robust immune responses after a single dose, relative to conventional mRNA which typically requires multiple and 1,000-fold higher doses.

Accordingly, repRNA vaccines were chosen as the vaccine candidates to stop a pandemic outbreak like COVID-19, as they have been studied with some experiences, often require only a single administration to be effective, and may have the potential of inducing protective levels of immunity rapidly with fewer and lower doses, while simultaneously reducing the load on manufacturing at scale.

Figure 7A:
FIGS. 7A-7C show the repRNA-CoV2S characterization in vitro.
Figure 7B:
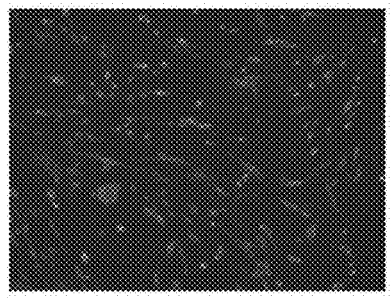
Figure 7C:
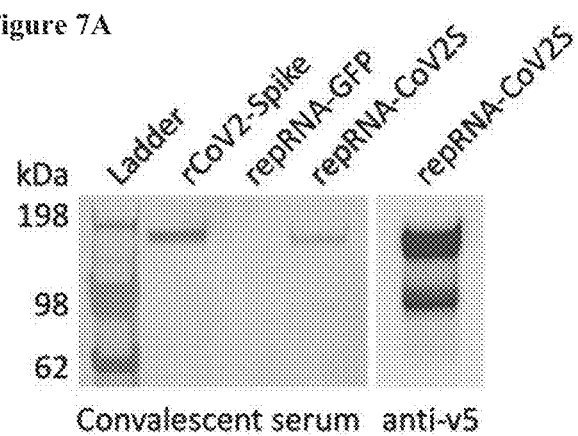

As shown in FIG. 7A, repRNAs incorporating sequences from the SARS-CoV-2 Spike (S) protein, including full length S (repRNA-CoV2S), were generated. Codon-optimized full length spike (S) open reading frame, including the S1-, S2-, transmembrane-(TM), and cytoplasmic-(CD) domains, corresponding to positions 21,536 to 25,384 in SARS-CoV-2 isolate Wuhan-Hu-1 (GenBank: MN908947.3), fused to a c-terminal v5 epitope tag, was cloned into an alphavirus replicon encoding the 4 nonstructural protein (nsP1-4) genes of Venezuelan equine encephalitis virus, strain TC-83. Following RNA transcription and capping, repRNA-COV2S, was transfected into BHK cells. Twenty four hours later, cells were analyzed by anti-v5 immunofluorescence and western blot using either convalescent human serum or anti-v5 for immunodetection, using recombinant SARS-CoV2 spike protein (rCoV2-Spike) and repRNA-GFP as positive and negative controls, respectively. The results in FIGS. 7B and 7C show the efficient expression of the v5-tagged S protein in BHK cells. FIG. 7C also demonstrates the endogenous expression of an S protein in BHK cells, reactive with natural SARS-CoV-2 immune sera, utilizing convalescent serum collected 29 days after onset of COVID-19 as an immunodetection reagent.

Formulation of repRNA-CoV2S with LION

Next, repRNA-CoV2S was formulated with an exemplary Lipid InOrganic Nanoparticle (LION), designed to enhance vaccine stability and intracellular delivery of the vaccine. The ability of LION/repRNA-CoV2S formulation to rapidly generate antibody and T cell responses was evaluated in mice.

Figure 8A:
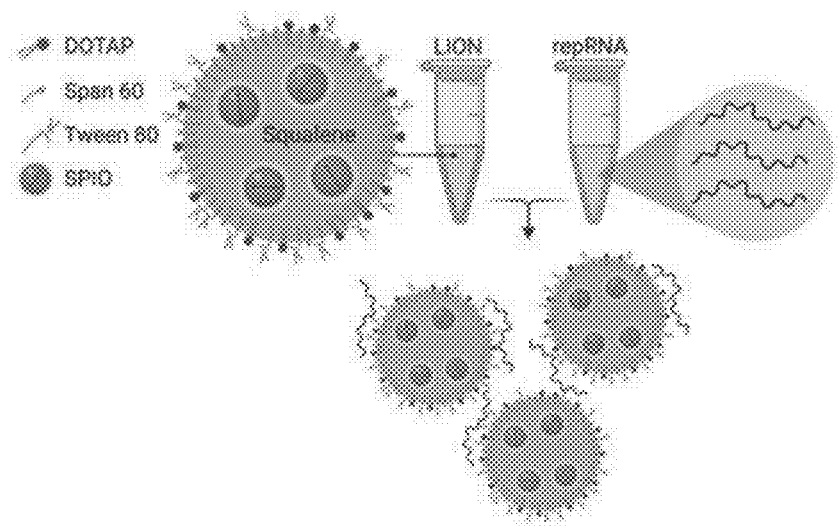
FIGS. 8A-8E show the exemplary Lipid InOrganic Nanoparticle (LION) formulation of repRNA.
Figure 8B:
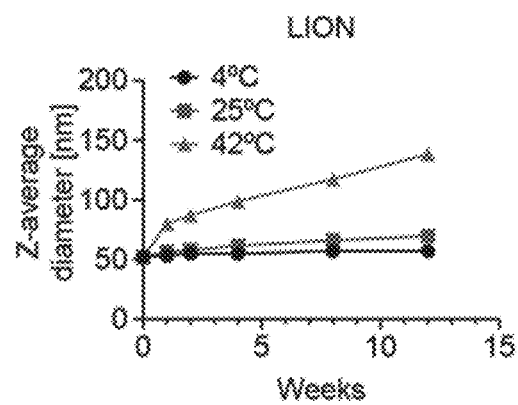

The general production techniques and materials for preparation of a LION composition followed those disclosed in Example 1. The exemplary LION is a highly stable cationic squalene emulsion with 15 nm superparamagnetic iron oxide ($Fe_3O_4$) nanoparticles (SPIO), embedded in the hydrophobic oil phase. FIG. 8A is a brief graphical representation of an exemplary LION and the formation of a vaccine complex after mixing LION with repRNA. Squalene is a vaccine adjuvant. SPIO nanoparticles have clinical usage in MRI contrast and intravenous iron replacement therapy; the unique nonlinear magnetic properties of SPIOs have also enabled their novel usages in a range of imaging, targeting and therapy applications. The LION also contained the cationic lipid 1,2-dioleoyl-3-trimethylammonium propane (DOTAP), which enabled electrostatic association with RNA molecules when combined by a 1:1 (v/v) mixing step. As disclosed in Example 1, this exemplary LION had an intensity-weighted average diameter of 52 nm (PDI=0.2), measured by dynamic light scattering (DLS). As shown in FIG. 8B, the LION formulation was colloidally stable for at least 3 months when stored at 4 and 25° C.

Figure 8C:
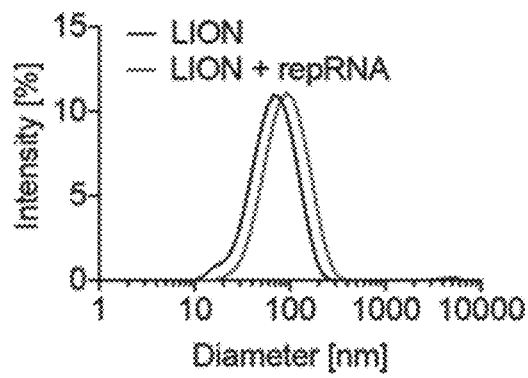
Figure 8D:
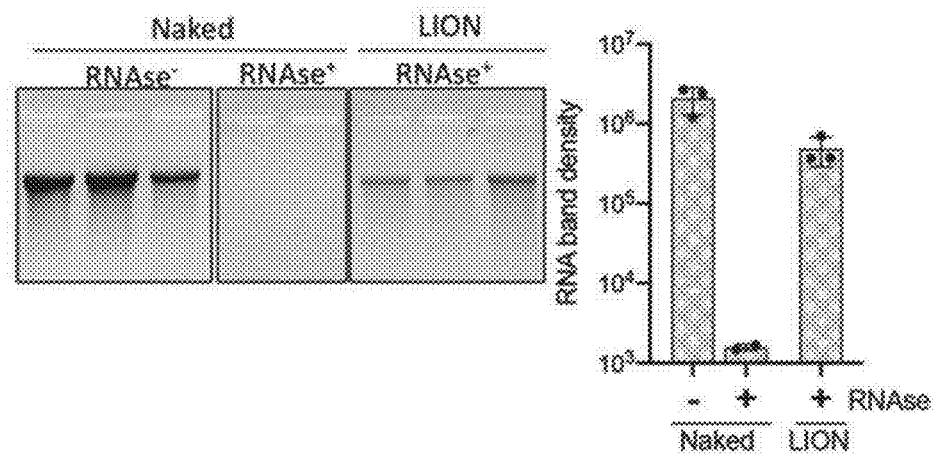
Figure 8E:
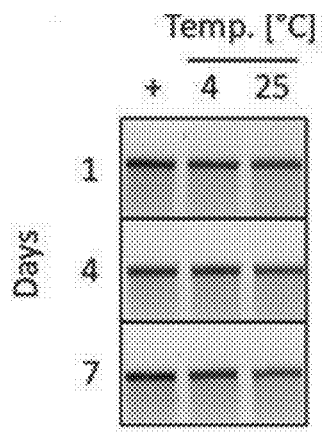
Figure 8F:
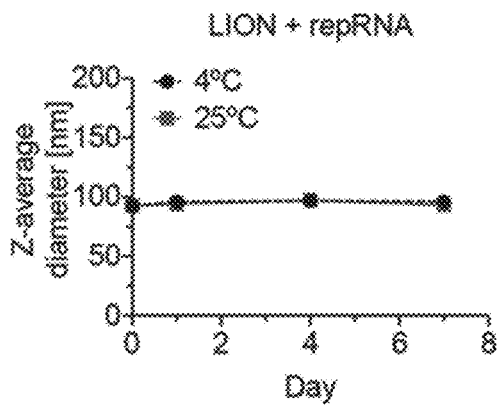
FIG. 8F shows the particle size of the complex. Data in FIG. 8B, FIG. 8E, and FIG. 8F are from a single experiment, while data in FIG. 8C and FIG. 8D are representative of three independent experiments. Data in FIG. 8B, FIG. 8D, and FIG. 8F are shown as mean±s.d. of 3 technical replicates.

When mixing LION with repRNA, electrostatic association between anionic repRNA and cationic DOTAP molecules on the surface of LION promotes immediate complex formation. The formation of LION-repRNA complex was confirmed by the increase in particle size to an intensity-weighted average diameter of 90 nm, detected by DLS (see FIG. 8C). As shown in FIG. 8D, the gel electrophoresis analysis of LION-formulated repRNA molecules extracted by phenol-chloroform treatment after a concentrated RNase challenge showed substantial protection from RNase-catalyzed degradation, as compared to the unformulated repRNA (Naked). To evaluate the short-term stability of the formulated vaccine, the repRNA integrity and complex stability were evaluated on 1, 4 and 7 days after mixing and storage at 4° C. and 25° C., as determined by gel electrophoresis of repRNA extracted by phenol-chloroform treatment and particle size of the complex. As shown in FIGS. 8E and 8F, LION maintained full integrity of the repRNA molecules (FIG. 8E) and the complex maintained its size (FIG. 8F) at all time points, indicating that the formulated vaccine complex was stable for at least a week after mixing.

LION/repRNA-CoV2S Delivery in Mice

Figure 9A:
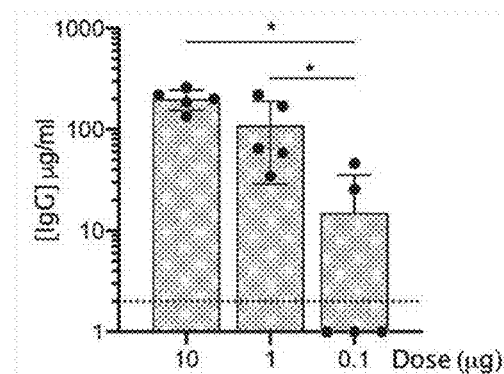
FIGS. 9A-9F show that the LION/repRNA-CoV2S complex induced Th1-biased and neutralizing antibodies in C57BL/6 mice. Six to eight-week old C57BL/6 mice (n=5/group) received 10, 1, or 0.1 µg LION/repRNA-CoV2S via the intramuscular route. Fourteen days after prime immunization, serum was harvested.
Figure 9B:
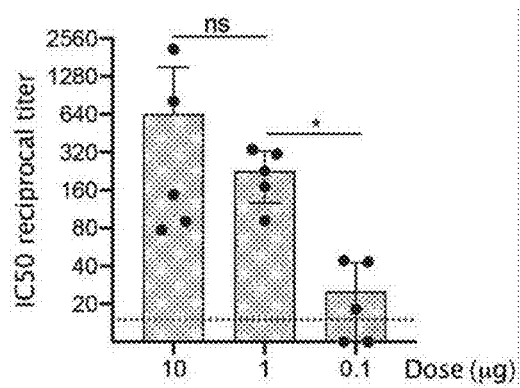
Figure 9C:
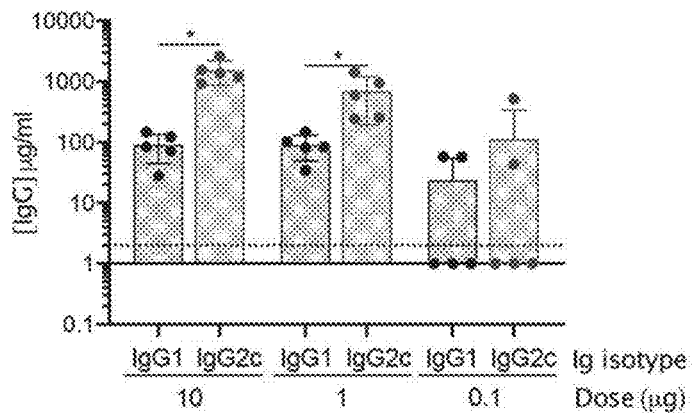
Figure 9D:
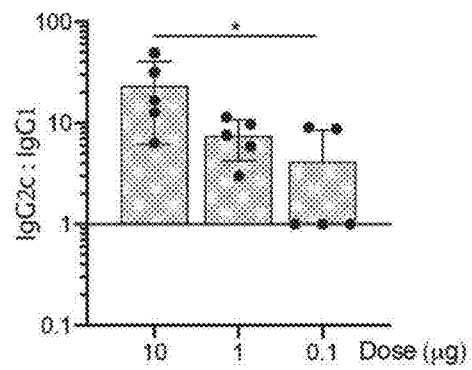

The LION/repRNA-CoV2S complex was administered to mice. Six to eight-week old C57BL/6 mice (n=5/group) received 10, 1, or 0.1 µg LION/repRNA-CoV2S via the intramuscular route. Fourteen days after prime immunization, serum was harvested. As shown in FIG. 9A, a single intramuscular immunization of C57BL/6 mice with 10 or 1 µg of LION/repRNA-CoV2S induced 100% seroconversion by 14 days post-immunization and robust anti-S IgG levels with mean binding titers of 200 and 109 µg/ml, respectively, and partial seroconversion (2 out of 5) at a 0.1 µg dose. As shown in FIG. 9B, both the 10 and 1 µg prime-only doses induced neutralizing antibodies with mean 50% inhibitory concentrations (IC50) of 1:643 and 1:226, respectively, as measured by pseudovirus neutralization assay (SARS- CoV-2 Wuhan-Hu-1 pseudotype). While all doses induced Th1-biased immune responses, as indicated by significantly higher IgG2c responses when compared to IgG1 (see FIG. 9C), there was a trend toward higher doses inducing even more Th1-biased responses, as indicated by higher IgG2c: IgG1 ratios (see FIG. 9D).

Figure 9E:
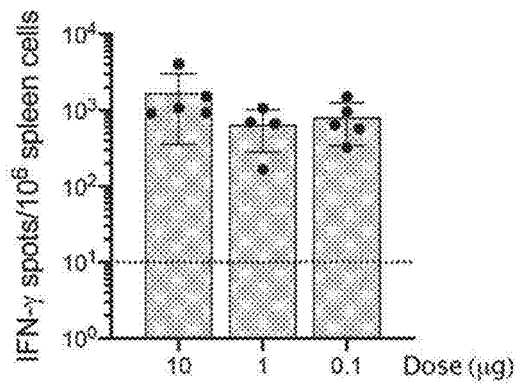
Figure 9F:
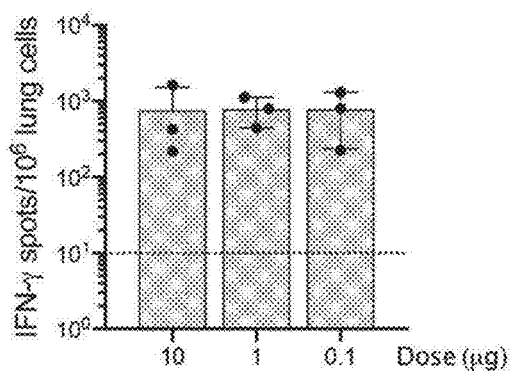

Given the potential role for T cells to contribute to protection, as seen with SARS and MERS, especially in the presence of waning antibody and memory B cell responses, T cell responses to LION/repRNA-CoV2S were also evaluated in mice. On day 28, this same cohort of mice received a second immunization. Twelve days later, spleens and lungs were harvested and stimulated with an overlapping 15-mer peptide library of the S protein, and the IFN-γ responses were measured by enzyme-linked immune absorbent spot (ELISpot) assay. As shown in FIG. 9E, the mice receiving a 10, 1, and 0.1 μg prime/boost exhibited robust splenic T cell responses with mean IFN-γ spots/106 cells of 1698, 650, and 801, respectively. Robust T cell responses were also detected in the lung and were similar between groups with mean IFN-γ spots/106 cells of 756, 784, and 777, respectively (see FIG. 9F).

Figure 10A:
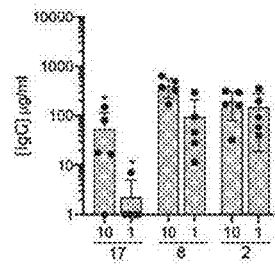
FIGS. 10A-10C show that the LION/repRNA-CoV2S complex induced Th1-biased antibodies in aged BALB/C mice. Two-, eight-, or seventeen-month old BALB/C mice (n-5/group) received 10 or 1 µg LION/repRNA-CoV2S via the intramuscular route. Fourteen days after prime immunization, serum was harvested.
Figure 10B:
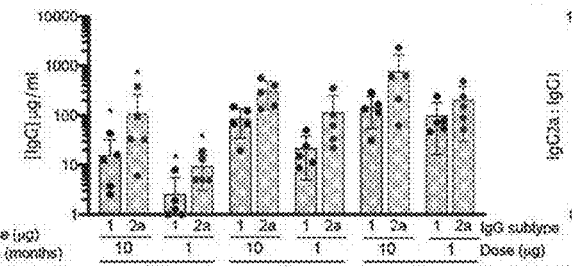
Figure 10C:
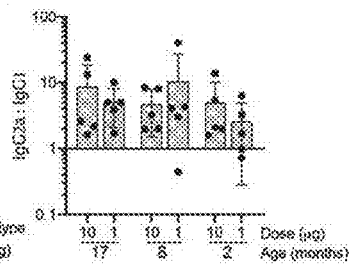

The elderly are among the most vulnerable to COVID-19, but the immune senescence in this population poses a barrier to an effective vaccination. To evaluate the effect of immune senescence on immunogenicity, 2-, 8-, or 17-month old BALB/C mice (n-5/group) received 10 or 1 μg LION/ repRNA-CoV2S via the intramuscular route. Fourteen days after the prime immunization, serum was harvested, and the anti-S IgG concentrations were measured. As shown in FIG. 10A, significantly lower antibody titers were observed in the 17-month old mice at both doses, when compared to the 2- and 8-month old mice, suggesting that higher doses and/or additional booster doses may be needed in the most immune-senescent populations to induce sufficient immunity. No differences were observed between the 2- and 8-month old mice. Although BALB/C mice tend to develop a more Th2 immune-biased response following vaccination, LION/repRNA-CoV2S induced the ratios of IgG2a:IgG1 of greater than 1 (see FIGS. 10B and 10C) in all age groups of the BALB/C mice, indicating a Th1-biased immune response. Given that severe, life-threatening COVID-19 appears to be more common among the elderly individuals, irrespective of type of T helper response, and that severe SARS is associated with skewing toward Th2 antibody profiles with an inadequate Th1 response, the ability of LION/repRNA-CoV2S to induce strong and Th1-biased responses in 8- and 2-month old mice, even in the Th2-biased BALB/c strain, provided positive signs regarding the safety and immunogenicity of this vaccine complex.

LION/repRNA-CoV2S Delivery in Nonhuman Primates

Having achieved a robust immunogenicity with the LION/repRNA-CoV2S complex in mice, immunization of pigtail macaques (Macaca nemestrina) was then carried out to determine if the vaccine complex was capable of inducing strong immune responses in a nonhuman primate model that more closely resembles humans in the immune response to vaccination.

Figure 11A:
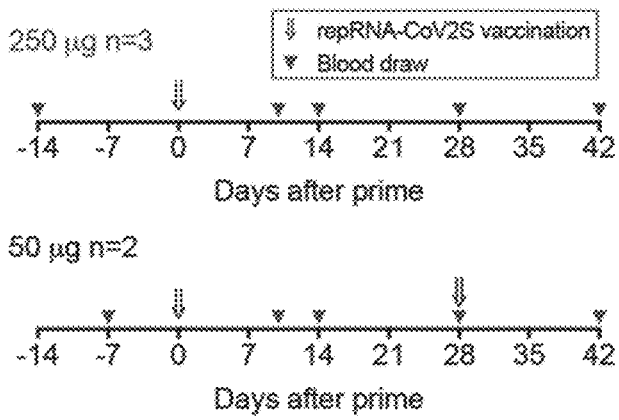
FIGS. 11A-11D show that a single dose of the LION/repRNA-CoV2S complex induced neutralizing antibody responses in pigtailed macaques.

In the dosage regime shown in FIG. 11A, three macaques received the LION/repRNA-CoV2S complex at a single 250 μg dose at week 0 via the intramuscular route, and two macaques received a 50 μg prime dose at week 0 and a boost dose at week 4 via the intramuscular route. Blood was collected 10, 14, 28, and 42 days post vaccination to monitor vaccine safety and immunogenicity. The 50 μg group received a boost vaccination on day 28, with the blood being collected 14 days later. There were no observed reactions at the vaccine injection site nor adverse reactions in the animals up to 42 days post-prime vaccination.

Figure 11B:
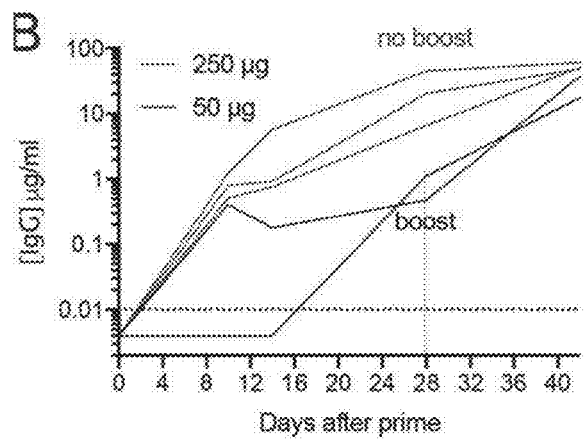
Figure 11C:
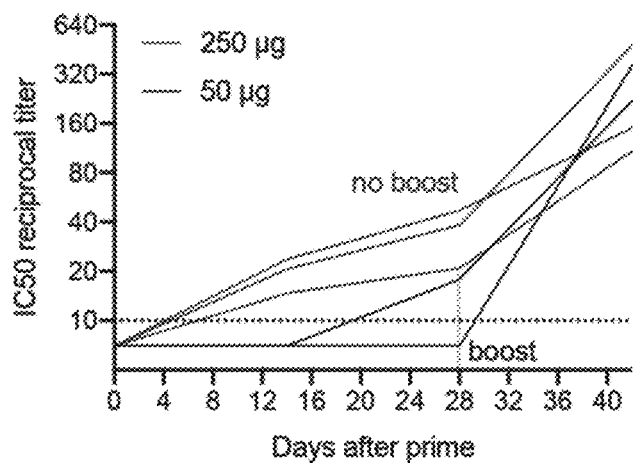

As shown in FIG. 11B, the ELISA analyses of sera collected 10, 14, 28, and 42 days after prime immunization, against the baseline established by the pre-immunization blood draws, showed that all three macaques immunized with the single 250 μg dose seroconverted as early as day 10, with anti-S IgG concentrations continuing to increase in these three animals to 48, 51, and 61 μg/ml by day 42. Both macaques receiving 50 μg repRNA-CoV2S seroconverted after a single dose, but developed significantly lower antibody responses with anti-S IgG concentrations of 1 and 0.5 μg/ml by day 28, as compared to 7, 20, and 45 μg/ml in the 250 μg group at this same time point (see FIG. 11B). However, 14 days after a booster immunization, the 50 μg group developed similar levels of anti-S IgG concentrations (18 and 37 μg/ml) as the 250 μg prime-only group at this time point (48, 51, and 61 μg/ml) (see FIG. 11B). Additionally, as shown in FIG. 11C, sera from the three macaques immunized with just the single 250 μg dose neutralized pseudovirus (SARS-CoV-2 Wuhan-Hu-1 pseudotype) transduction of cells in vitro with reciprocal IC50 titers of 1:38, 1:20 and 1:47 by day 28 with levels increasing to 1:472, 1:108, and 1:149 by day 42, whereas the 50 μg group achieved similar robust IC50 titers only after the booster immunization reaching pseudovirus IC50 titers of 1:218 and 1:358 by day 42.

Figure 11D:
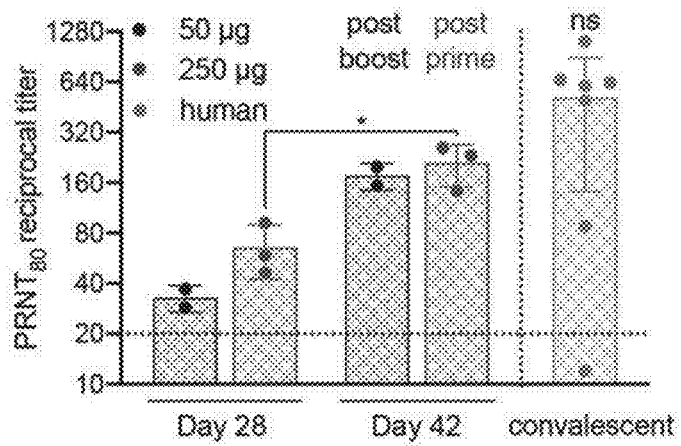

Sera collected 28- and 42-days post vaccination were further analyzed for neutralization of wild type SARS-CoV-2/WA/2020 by 80% plaque reduction neutralization test (PRNT80) and compared to neutralizing titers in sera from convalescent humans collected 15-64 days following natural infection. As shown in FIG. 11D, a single immunization with 50 and 250 μg of LION/repRNA-CoV2S induced mean PRNT80 titers of 1:32 and 1:66 by day 28, respectively. By Day 42, mean PRNT80 titers significantly increased to 1:176 after a booster immunization in the 50 μg group and to 1:211 in the prime-only 250 μg group. All 5 macaques developed PRNT80 titers within the same range as titers measured in the seven convalescent humans (<1:20 to 1:1280, collected 15 to 64 days post onset) and there was no significant difference in mean neutralizing titers between all 5 vaccinated macaques (1:197) and convalescent humans (1:518) (P=0.27, FIG. 11D). Recently, serum-neutralizing titers, measured as the IC50 titer that neutralized SARS-CoV-2 by 50% tissue culture infectious dose (TCID50), were reported in rhesus macaques that were either re-infected or challenged after vaccination with an inactivated SARS-CoV-2 vaccine. In the former report, IC50 titers as low as 1:8 were associated with protection from re-infection, while in the latter, IC50 titers as low as 1:50 were associated with reduced viral load and protection from lung pathology. These data suggest that a 250 μg prime-only or a 50 μg prime/boost immunization with the LION/repRNA-CoV2 vaccine would be able to induce levels of neutralizing antibodies sufficient to protect nonhuman primates from infection and disease.

RepRNA vaccines against a variety of infectious diseases and cancers have been shown to be safe and potent in clinical trials, and the cell-free and potentially highly scalable manufacturing process of repRNA, when used with effective synthetic formulations, such as LION, presented further benefits over mRNA. The two-vial approach would provide a significant manufacturing and distribution advantage over LNP formulations that encapsulate RNA, as the vaccine can be stockpiled and combined onsite as needed. Additionally, the LION/repRNA-CoV-2 complex induced robust S-specific T cell responses in mice. Following natural infection of humans with the related SARS-CoV, neutralizing antibody and memory B cell responses in some individuals are reported to be short lived (~3 years) while memory T cells persist at least 6 years (53), suggesting a potential role for T cells in long term responses especially in those who lack robust memory B cell responses. Additionally, anti-S T-cell responses to the related SARS- and MERS-CoVs contribute towards viral clearance in normal as well as aged mice infected with SARS- or MERS-CoV, respectively.

In sum, these results demonstrate a great potential for the LION/repRNA-CoV2S, complex to induce a rapid immune protection from SARS-CoV-2 infection. A scalable and widely distributed vaccine capable of inducing robust immunity in both young and aged populations against SARS-CoV-2 infection in a single shot would provide immediate and effective containment of the pandemic. Critically, the vaccine induced Th1-biased antibody and T cell responses in both young and aged mice, an attribute that has been associated with improved recovery and milder disease outcomes in SARS-CoV-infected patients. A single-dose administration in nonhuman primates elicited antibody responses that potently neutralized SARS-CoV-2. These data support the potential of the LION/repRNA-CoV2S complex as a vaccine for protection from SARS-CoV-2 infection.

Example 8. Using LION Formulations for Vaccine Delivery in Rabbits

Animals: 8 New Zealand White rabbits (Oryctolagus cuniculus), 4 males and 4 females, were separated into two groups, of each 2 males and females. Group 1 was injected with high dose LION-RNA formulation (250 µg repRNA with LION formulation) and Group 2 was injected low dose LION-RNA formulation (10 µg repRNA with LION formulation).

Vaccine Preparation: LION carrier and repRNA-CoV2S were complexed at a nitrogen-to-phosphate molar ratio of 15 in 10 mM sodium citrate and 20% sucrose buffer and were delivered to the study animals in three 0.5 mL intramuscular dosages, two weeks apart.

ELISA: Antigen-specific IgG responses were detected by ELISA using recombinant SARS-CoV-2S as the capture antigen. ELISA plates (Nunc, Rochester, NY) were coated with 1 µg/mL antigen or with serial dilutions of purified polyclonal IgG to generate a standard curve in 0.1 M PBS buffer and blocked with 0.2% BSA-PBS. Then, in consecutive order, following washes in PBS/Tween, serially diluted serum samples, anti-rabbit IgG-HRP (Southern Biotech, Birmingham, AL), and TMB peroxidase substrate were added to the plates, followed by quenching with HCl. Plates were analyzed at 405 nm (ELX808, Bio-Tek Instruments Inc, Winooski, VT). Absorbance values from each serum dilution point were used to calculate titers.

Figure 12:
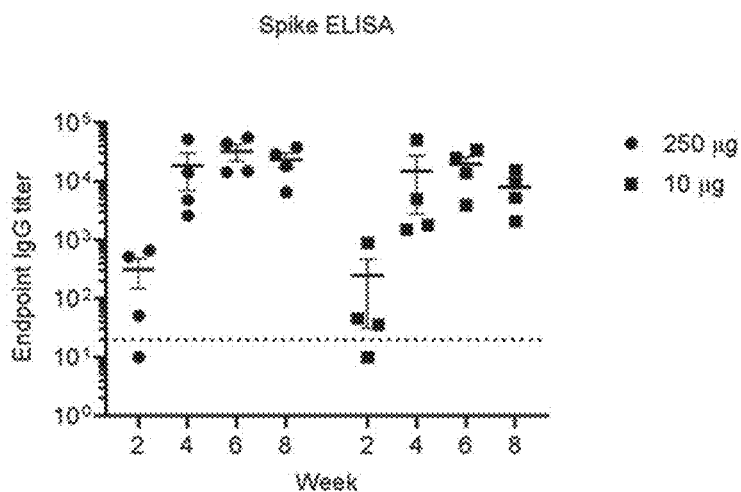
FIG. 12 shows the anti-spike IgG levels in the rabbits injected intramuscularly with repRNA-SARS-CoV2S (at 250 µg and 10 µg dose level, respectively) formulated with LION formulation. Rabbits were bled at regular intervals after intramuscular injection, and protein expression was determined by assaying IgG concentrations by anti-Spike ELISA. Each point represents data from an individual animal. Data are displayed as mean and SEM, n=4 per group.

FIG. 12 shows the anti-spike IgG levels in the rabbits injected intramuscularly with repRNA-SARS-CoV2S (at 250 µg and 10 µg dose level, respectively) formulated with LION formulation. As shown in the example, animals rapidly mounted an immune response to the injected vaccine. At week 4 in both dose levels, antibody titers nearly plateaued and did not increase significantly in weeks 6 or 8.

Example 9. Using LION Formulations for Vaccine Delivery—RSV Vaccine

Figure 13A:
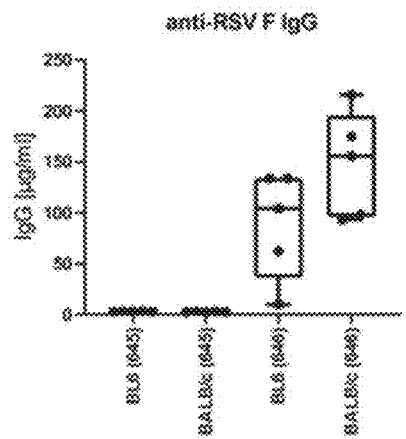
FIG. 13A shows the anti-F IgG levels in C57Bl/6 and BALB/c mice injected intramuscularly with 2.5 µg repRNA-RSV complexed with a LION formulation.

RSV repRNA (2.5 µg) complexed with a LION formulation was administered intramuscularly in C57Bl/6 and BALB/c mice. Mice blood was collected 28 days after intramuscular injection, and protein expression was determined by assaying Anti-F IgG concentrations by ELISA. The results of anti-F IgG levels in the serum of the C57Bl/6 and BALB/c mice are shown in FIG. 13A. As shown in FIG. 13A, RVS G protein-specific responses were induced by replicon 646 in both C57BL/6 and BALB/c mice.

Figure 13B:
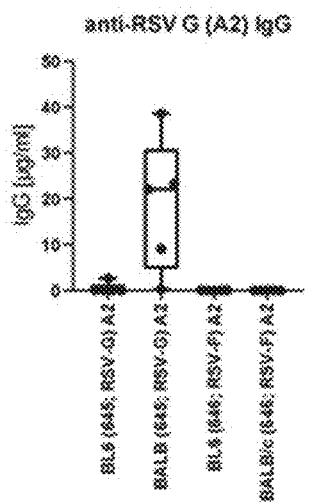
FIG. 13B shows the anti-G (A2) IgG levels in C57Bl/6 and BALB/c mice injected intramuscularly with 2.5 µg repRNA-RSV complexed with a LION formulation. Blood was collected 28 days after intramuscular injection, and the serum was prepared and assessed by ELISA. Replicon number (645 or 646) is indicated in the parentheses. Each point represents data from an individual animal, with the whiskers representing minimum to maximum, the box representing the interquartile range and the horizontal bar depicting the median.

RSV repRNA (2.5 µg) complexed with a LION formulation was administered intramuscularly in C57Bl/6 and BALB/c mice. Mice blood was collected 28 days after intramuscular injection, and protein expression was determined by assaying Anti-G (A2) IgG concentrations by ELISA. The results of anti-G (A2) IgG levels in the serum of the C57Bl/6 and BALB/c mice are shown in FIG. 13B. As shown in FIG. 13B, RVS G A2 strain protein-specific responses were induced by replicon 645 in only BALB/c mice.

Example 10. Using LION Formulations for Delivery of Immunomodulating RNA LION Formulations Protect Immunomodulating RNA PAMP from RNases An RIG-I agonist, PAMP, was formulated with an exemplary LION formulation (15 nm, similar to 79-006A in Example 1). The general production techniques and materials for preparation of a LION composition followed those disclosed in Example 1.

Figure 14A:
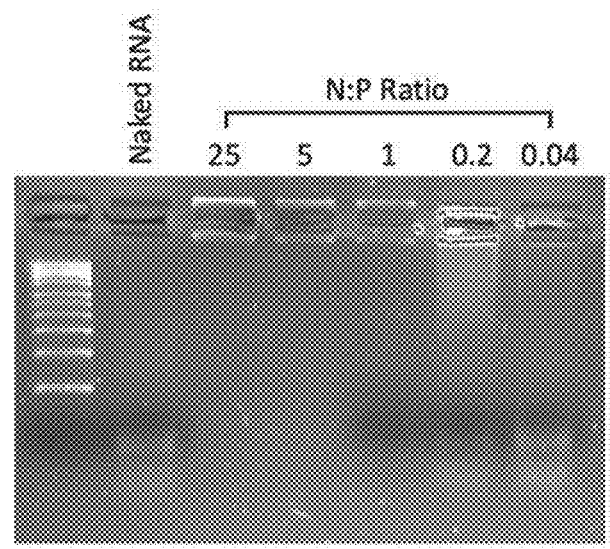
FIGS. 14A-14B show the binding of PAMP to the LION formulation that provided protection from RNase challenge.
Figure 14B:
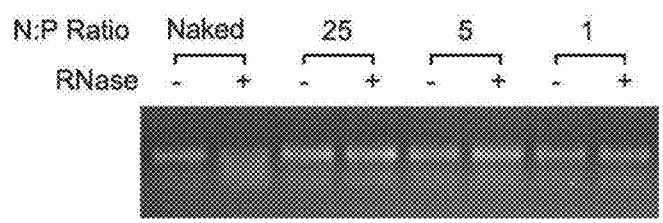

FIG. 14A-14B show the binding of PAMP to the LION formulation that provided protection from RNase challenge. FIG. 14A shows the gel electrophoresis analysis of PAMP-LION complexes at various N:P complexing ratios (0.04, 0.2, 1, 5, and 25, respectively) run on an RNA gel and was assessed for free RNA. As shown in FIG. 14A, free RNA was not present for PAMP-LION formulations at N:P ratio of 1, 5 and 25. FIG. 14B shows the gel electrophoresis analysis of PAMP-LION complexes, following a challenge with RNase A, as compared to naked PAMP (unformulated PAMP). RNA was extracted from LION and run on an agarose gel to assess RNA degradation. The results show complexing of PAMP to LION protected the RNA from RNase-catalyzed degradation, as compared to the unformulated RNA (Naked).

Immune Stimulation of a RIG-I Agonist, PAMP, Delivered by LION

This example illustrates the immune stimulation of the RIG-I agonist, PAMP, delivered by the LION formulation, when the PAMP-LION complex was added to A549-Dual cells. A549-Dual cells contain two reporter constructs: the IFN-β promoter that drives the expression of SEAP, and the IFIT2 promoter that drives the expression of luciferase.

Figure 15:
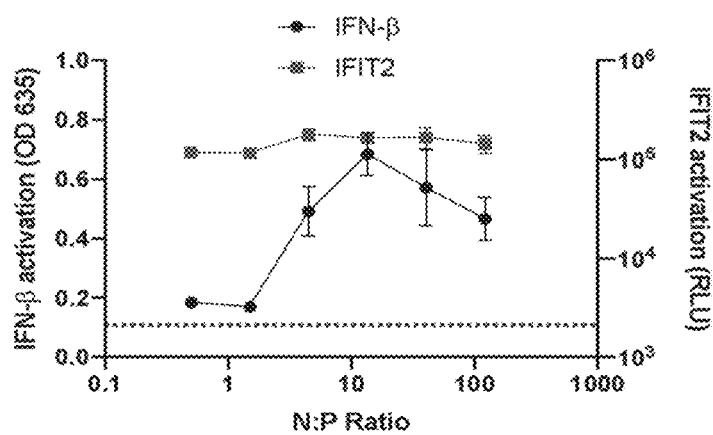
FIG. 15 shows the activation of the IFN-β promoter and IFIT2 measured by SEAP activity and luciferase activity in the supernatant, respectively, by the PAMP-LION complex as a function of N:P ratio. Dashed lines represent activation levels of PAMP alone.

PAMP was formulated with a LION formulation at various N:P complexing ratios (0.5, 1.5, 4.5, 13.5, 40.5, and 121.5), and 3.7 ng PAMP/LION was added to A549-Dual cells. FIG. 15 shows the activation of the IFN-β promoter and IFIT2 measured by SEAP activity and luciferase activity in the supernatant, respectively, by the PAMP-LION complex as a function of N:P ratio. The results show the innate immune stimulation of the RIG-I agonist, PAMP, delivered by the PAMP-LION formulations at all the N:P ratios, for both the IFN-β promoter and the IFIT2 promoter, although the N:P ratio at 4.5-40.5 appeared to provide better immune stimulations for the IFN-β promoter.

Immune Stimulation of a RIG-I Agonist and TLR3 Agonist Delivered by LION

This example illustrates the immune stimulation of a RIG-I agonist, PAMP, and a TLR3 agonist, Riboxxim, delivered by the LION formulation, when the RNA-LION complex was added to A549-Dual cells.

Figure 16A:
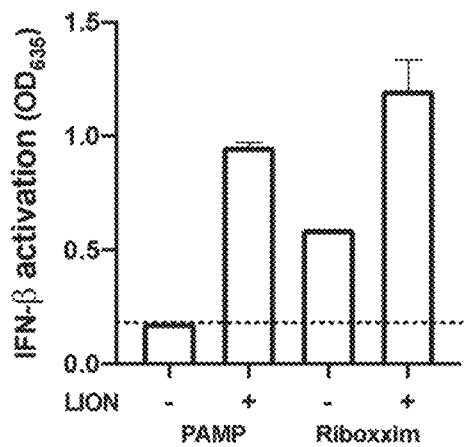
FIGS. 16A and 16B show the activation of the IFN-β promoter (FIG. 16A) and IFIT2 (FIG. 16B) measured by SEAP activity and luciferase activity in the supernatant, respectively, by the PAMP-LION formulation or Riboxxim-LION formulation, as compared to unformulated RNA. The dashed lines represent OD$_{635}$ readings of media control wells.
Figure 16B:
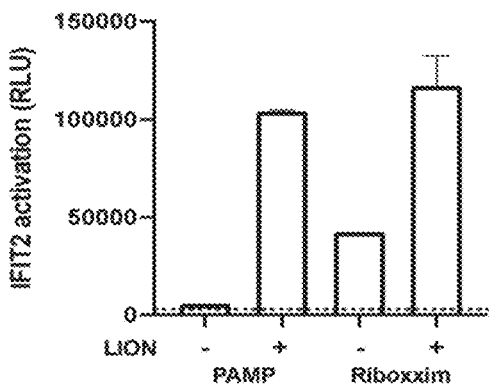

PAMP (a RIG-I agonist) or Riboxxim (a TLR3 agonist), unformulated (naked control) or formulated with a LION formulation at a N:P ratio of 8, was added to A549-Dual cells. FIGS. 16A and 16B show the activation of the IFN-β promoter (FIG. 16A) and IFIT2 (FIG. 16B) measured by SEAP activity and luciferase activity in the supernatant, respectively, by the PAMP-LION formulation or Riboxxim-LION formulation, as compared to unformulated RNA. The results show the innate immune stimulation of both the RIG-I agonist, PAMP, and the TLR3 agonist, Riboxxim, delivered by complexing with the LION formulations worked to induce innate immune activation, triggering robust levels of reporter protein expression as compared to their unformulated naked control.

Figure 16C:
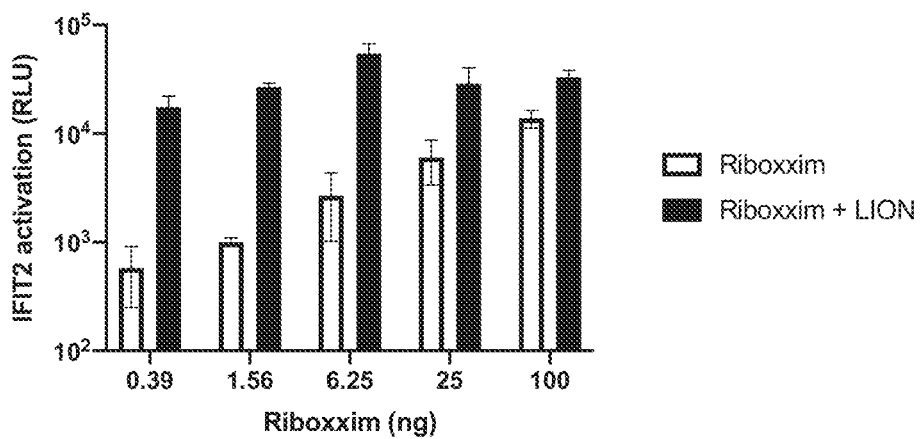
FIG. 16C shows the activation of the IFIT2 by the Riboxxim-LION formulation, as compared to unformulated Riboxxim, as a function of the Riboxxim dose level.

FIG. 16C shows the activation of the IFIT2 by the Riboxxim-LION formulation, as compared to unformulated Riboxxim, as a function of the Riboxxim dose level. The results show that, at all tested dose levels, the LION formulations complexed with Riboxxim induced a higher level of IFIT2 activation as compared to its unformulated naked control, although the Riboxxim-LION formulation with a higher dose level induced a stronger IFIT2 activation.

This example illustrates the immune stimulation of the RIG-I agonist, PAMP, delivered by the LION formulation, when the PAMP-LION complex was delivered intranasally to C57BL/6 mice. PAMP was formulated with a LION formulation at an N:P ratio of 8, and 0.2, 1, or 5 µg PAMP/LION was delivered into the nares of C57BL/6 mice. Eight hours later, nasal cavities and lungs of the mice were removed and immediately frozen, then the RNA was extracted and subjected to PCR for various target genes.

Figure 16D:
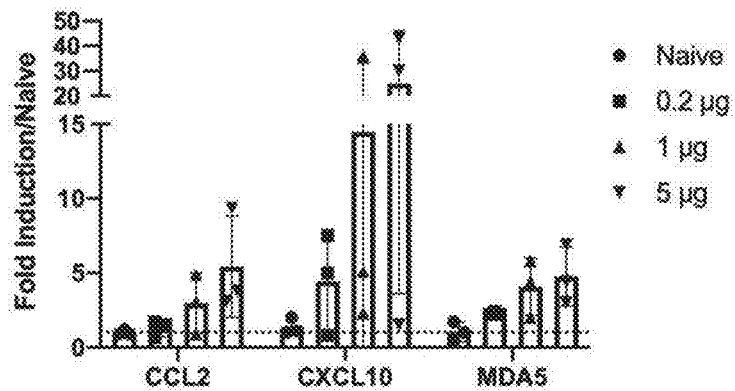
FIG. 16D shows the dose-dependent induction of innate immune genes in the nasal cavity of treated mice compared to naïve controls.
Figure 16E:
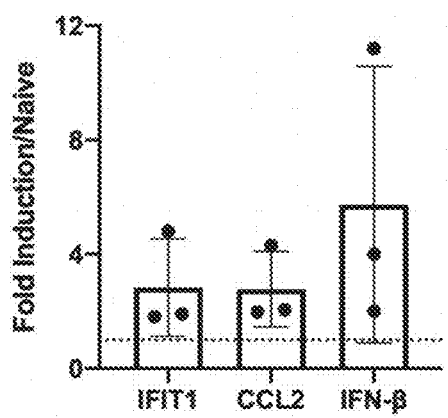
FIG. 16E shows the activation of innate immune genes in the lungs of treated mice.
Figure 16F:
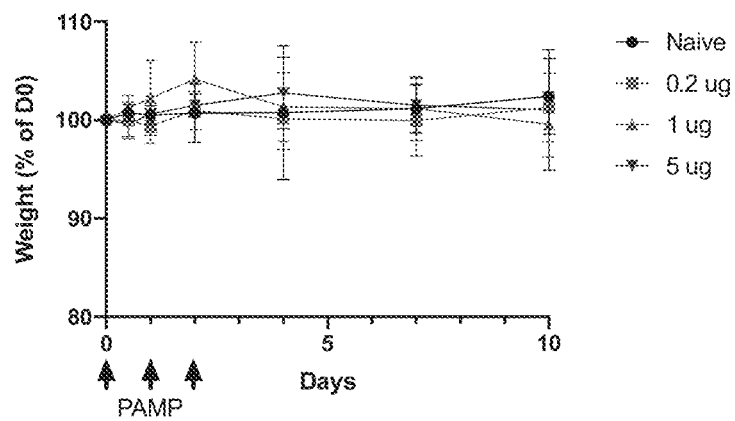
FIG. 16F shows that the mice maintained body weight when being administered the PAMP:LION formulation intranasally for 3 consecutive days.

FIG. 16D shows the dose-dependent induction of innate immune genes in the nasal cavity of treated mice compared to naïve controls. FIG. 16E shows the activation of innate immune genes in the lungs of treated mice. FIG. 16F shows that the mice maintained body weight when being administered the PAMP:LION formulation intranasally for 3 consecutive days.

These results demonstrate that LION supported the delivery of bioactive PAMP by intranasal inoculation; at all tested dose levels, the LION formulations complexed with PAMP upregulated the protein expression in the nasal cavity and the lung when the formulation was delivered intranasally to mice.

Example 11. Production of Lipid Inorganic Nanoparticles (LIONs) with Aluminum Hydroxide Core Labelled as 108-011

These LIONs comprise 37.5 mg/ml squalene, 37 mg/ml Span® 60, 37 mg/ml Tween® 80, 30 mg/ml DOTAP chloride, TOPO-coated Al(OOH) (Alhydrogel® 2%) particles at a target concentration of 1 mg Al/ml and 10 mM sodium citrate dihydrate. The LION particles were manufactured using the following procedures.

In a 50 ml centrifuge tube, 10 ml of Alhydrogel® was added and centrifuged at 300 rpm for 3 minutes. The supernatant water was removed and replaced with an equal amount of methanol. The particles were centrifuged again at 300 rpm for 3 minutes and the methanol supernatant was removed and replaced with an equal amount of methanol. This procedure was repeated an additional two times to remove residual water and to re-suspend the Alhydrogel® particles in 10 ml of methanol. The zeta potential of Alhydrogel® dispersed in methanol was +11.5 mV. To this dispersion, 1 ml of 250 mg/ml trioctylphosphine oxide (TOPO) was added and the mixture was left overnight in an orbital shaker maintained at 37° C. and 250 rotations per minute. This was done to coat a layer of TOPO on the surface of Alhydrogel® by ligand exchange reaction. The excess TOPO in the dispersion was removed by washing with methanol. The zeta potential of the TOPO-coated Al(OOH) particles was recorded to be +5 mV. The reduction in zeta potential indicates the surface modification of Alhydrogel® with TOPO was successful. This process was done to convert the hydrophilic surface of Alhydrogel® to hydrophobic, thus facilitating the miscibility of Alhydrogel® in the 'oil' phase of LION. Methanol in the TOPO coated Al(OOH) dispersion was evaporated in the fume hood for 45 minutes at 55 degree Celsius leaving a dry coat of TOPO-Al(OOH) particles. To the dried TOPO-Al(OOH) particles, 3.7 grams of Span® 60, 3.75 grams of squalene and 3.0 grams of DOTAP chloride were added to prepare the "oil" phase. The oil phase was sonicated 45 minutes in a water bath pre-heated to 65° C.

Separately, in a 1-liter glass bottle, the "aqueous" phase was prepared by adding 19.5 grams of Tween® 80 to 500 ml of 10 mM sodium citrate dihydrate solution prepared with Milli-Q water. The aqueous phase was stirred for 30 minutes to allow complete dissolution of Tween® 80. After complete dissolution of Tween® 80, 92 ml of the aqueous phase was transferred to a 200 ml beaker and incubated in a water bath pre-heated to 65° C.

To the heated oil phase, 92 ml of the pre-heated aqueous phase was added. The mixture was immediately emulsified using a VWR® 200 homogenizer (VWR International) until a homogenous colloid with a milk-like appearance was produced. The colloid was subsequently processed by passaging the fluid through a Y-type interaction chamber of a M110-P microfluidizer at 30,000 psi. The fluid was passaged 17 times until the z-average hydrodynamic diameter, measured by dynamic light scattering (Malvern Zetasizer Ultra), was 61.9 nm with a 0.24 polydispersity index. The microfluidized LION sample was terminally filtered with a 200 nm pore-size polyethersulfone (PES) syringe filter.

Table 2 summarizes the size and PDI of the resulting Alum-LION nanoparticles before and after complexing with alphavirus-derived replicon RNA molecules. Table 3 below summarizes the characteristics of the resulting Alum-LION nanoparticles.

TABLE 2

Size and PDI of Alum-LION before and after complexing with alphavirus-derived replicon RNA molecules. Values below are mean of three technical replicates.

| Size of Alum-LION before complexing | | Size of Alum-LION after complexing | | PDI of Alum-LION before complexing | | PDI of Alum-LION after complexing | |
| --- | --- | --- | --- | --- | --- | --- | --- |
| Size (nm) | SD | Size (nm) | SD | PDI | SD | PDI | SD |
| 61.92 | 0.488 | 95.48 | 2.129 | 0.241 | 0.003 | 0.271 | 0.009 |

TABLE 3

Characterization of the Alum-LION formulation.

| Property | Method | Value |
|---|---|---|
| Particle size (Z-average) | Dynamic Light Scattering; mean ± SD of three technical replicates | 61.92 ± 0.5 nm |
| Size distribution (PDI) | Dynamic Light Scattering; mean ± SD of three technical replicates | 0.241 ± 0.003 |
| Zeta potential | Dynamic Light Scattering; mean ± SD of five technical replicates | 34.98 ± 2.47 mV |
| Aluminum concentration | Inductively coupled plasma-optical emission spectroscopy; mean ± SD of three sample replicates | 598 ± 14 µg/ml |
| DOTAP concentration | Reversed phase-High performance liquid chromatography; mean ± SD of three sample replicates | 20.37 ± 0.57 mg/ml |
| Squalene concentration | Reversed phase-High performance liquid chromatography; mean ± SD of three sample replicates | 26.38 ± 0.60 mg/ml |

Example 12. RNA Delivery with Exemplary LION Formulations

A VEE replicon RNA containing the nLuc sequence in the subgenome was diluted to 6.4 ng/L and complexed to LION at an N:P ratio of 15 for 30 minutes on ice. Two types of LION formulations were used: one having the 15-nm iron oxide ($Fe_3O_4$) nanoparticles (SPIO) as the core (similar to 79-006A prepared according to Example 1), and the other having the TOPO-coated aluminum oxyhydroxide nanoparticles as the core, prepared according to Example 11.

The RNA:LION complex was diluted 1:10 in buffer (10% sucrose, 5 mM NaCitrate), and 50 µL (16 ng RNA) was added to wells of a 96-well plate containing A549-Dual cells (Invivogen) in 150 µL Optimem. Cells were transfected for 4 hours, the media replaced with complete Dulbecco's Modified Eagle Medium (DMEM) (containing 10% fetal bovine serum, L-glutamine, and Penicillin/Streptomycin), and incubated overnight at 37° C. with 5% $CO_2$. The following day, the media was removed and nLuc expression was assessed using the Nano-Glo Luciferase Assay System (Promega) according to the manufacturer's instructions. Plates were read using a Spectramax i3 plate reader (Molecular Devices).

Figure 17:
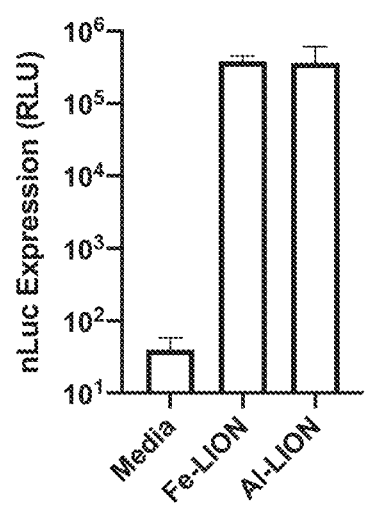
FIG. 17 shows in vitro protein expression from exemplary RNA:LION complexes with replicon RNA encoding nLuc, using SPIO (Fe-LION) or TOPO-coated aluminum oxyhydroxide nanoparticles (Al-LION) as the core of the LION formulation.

FIG. 17 shows the resulting in vitro protein expression from the RNA:LION complexes with replicon RNA encoding nLuc, using SPIO (Fe-LION) or TOPO-coated aluminum oxyhydroxide nanoparticles (Al-LION) as the core of the LION formulation. The figure demonstrates that both LION formulations containing either the iron oxide nanoparticles or aluminum oxyhydroxide nanoparticles as the cores provided successful in vitro delivery of nLuc replicon, when the RNA was complexed with LION formulation.

All references disclosed herein, including patent references and non-patent references, are hereby incorporated by reference in their entirety as if each was incorporated individually.

It is to be understood that the terminology used herein is for the purpose of describing specific embodiments only and is not intended to be limiting. It is further to be understood that unless specifically defined herein, the terminology used herein is to be given its traditional meaning as known in the relevant art.

References throughout this specification to "one embodiment" or "an embodiment" and variations thereof means that a particular feature, structure, or characteristic described in connection with the embodiment are included in at least one embodiment, and are not necessarily all referring to the same embodiment. Furthermore, the particular features, structures, or characteristics may be combined in any suitable manner in one or more embodiments. The abbreviation "e.g." is used herein to indicate anon-limiting example, and is synonymous with the term "for example."

As used in this specification and the appended claims, the singular forms "a," "an," and "the" include plural referents, i.e., one or more, and the letter "s" following a noun designates both the plural and singular forms of that noun, unless the content and context clearly dictates otherwise. It should also be noted that the conjunctive terms, "and" and "or" are generally employed in the broadest sense to include "and/or," which is intended to encompass an embodiment that includes all of the associated items or ideas and one or more other alternative embodiments that include fewer than all of the associated items or ideas, unless the content and context clearly dictates inclusivity or exclusivity as the case may be.

In addition, where features or aspects of the invention are described in terms of Markush groups, it is intended that the invention embraces and is also thereby described in terms of any individual member and any subgroup of members of the Markush group, and Applicants reserve the right to revise the application or claims to refer specifically to any individual member or any subgroup of members of the Markush group.

Where a range of values is provided herein, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention. For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

What is claimed is:

1. A composition, wherein the composition comprises:
    DNA molecules, wherein the DNA molecules comprise a sequence encoding an antigen; and
    lipid nanoparticles, wherein noncomplexed lipid nanoparticles are characterized as having a z-average diameter particle size measurement of about 20 nm to about 60 nm when measured using dynamic light scattering, and wherein the lipid nanoparticles comprise:
    a surface comprising cationic lipids; and
    a hydrophobic core, wherein the hydrophobic core comprises liquid oil,
    wherein lipids present in the hydrophobic core are in liquid phase at 25 degrees Celsius, and wherein the DNA molecules are complexed to the cationic lipids to form DNA molecule-lipid nanoparticle complexes.

2. The composition of claim 1, wherein the antigen in derived from a virus, a bacterium, a protozoa, or a cancer.

3. The composition of claim 2, wherein the virus is a Human Immunodeficiency virus (HIV), a hepatitis virus, a Coronavirus, a Venezuelan equine encephalitis (VEE) virus, Zika virus.

4. The composition of claim 1, wherein the composition further comprises a TLR agonist, a RIG-I agonist, an RNA encoding a protein, a protein, a carbohydrate, a saponin, a viral fragment, or a cellular fragment.

5. The composition of claim 1, wherein the hydrophobic core further comprises a solid inorganic nanoparticle.

6. The composition of claim 5, wherein the solid inorganic nanoparticle has an average diameter from about 3 nm to about 50 nm.

7. The composition of claim 5, wherein the solid inorganic nanoparticle is selected from the group consisting of metal salts, metal oxides, metal hydroxides, and metal phosphates.

8. The composition of claim 5, wherein the solid inorganic nanoparticle comprises iron oxide.

9. The composition of claim 8, wherein the iron oxide is magnetite ($Fe_3O_4$), maghemite ($\gamma$-$Fe_2O_3$), wüstite (FeO), hematite ($\alpha$-$Fe_2O_3$), or any combination thereof.

10. The composition of claim 1, wherein the liquid oil is a vegetable oil, an animal oil, or a synthetically prepared oil.

11. The composition of claim 1, wherein the liquid oil is capric/caprylic triglyceride, vitamin E, lauroyl polyoxylglyceride, monoacylglycerol, squalene, or any combination thereof.

12. The composition of claim 1, wherein the liquid oil is squalene, sunflower oil, soybean oil, olive oil, grapeseed oil, capric/caprylic triglyceride, or any combination thereof.

13. The composition of claim 1, wherein the cationic lipid is selected from the group consisting of 1,2-dioleoyloxy-3-(trimethylammonium)propane (DOTAP); 3b-[N-(N',N'-dimethylaminoethane)-carbamoyl]cholesterol (DC Cholesterol); dimethyldioctadecylammonium (DDA); 1,2-dimyristoyl-3-trimethylammoniumpropane (DMTAP); dipalmitoyl(C16:0)trimethyl ammonium propane (DPTAP); distearoyltrimethylammonium propane (DSTAP); N-[1-(2,3-dioleyloxy)propyl]-N,N,N-trimethylammonium chloride (DOTMA); N,N-dioleoyl-N,N-dimethylammonium chloride (DODAC); 1,2-dioleoyl-sn-glycero-3-ethylphosphocholine (DOEPC);

1,2-dioleoyl-3-dimethylammonium-propane (DODAP); 1,2-dilinoleyloxy-3-dimethylaminopropane (DLinDMA); and 1, r-((2-(4-(2-((2-(bis(2-hydroxydodecyl)amino)ethyl) (2-hydroxydodecyl)amino)ethyl) piperazin-1-yl)ethyl)azanediyl)bis(dodecan-2-ol) (C 12-200).

14. The composition of claim 1, wherein the surface further comprises a hydrophobic surfactant and a hydrophilic surfactant.

15. The composition of claim 14, wherein the hydrophobic surfactant is selected from the group consisting of sorbitan monostearate, sorbitan monooleate, and sorbitan trioleate.

16. The composition of claim 14, wherein the hydrophilic surfactant comprises polyethylene oxide or polysorbate.

17. The composition of claim 16, wherein the polysorbate comprises polysorbate 80.

18. The composition of claim 1, wherein the DNA molecules further comprise a sequence encoding for an RNA polymerase complex region from an RNA virus.

19. The composition of claim 18, wherein the RNA polymerase complex region comprises sequence from a Venezuelan equine encephalitis virus.

20. The composition of claim 19, wherein the Venezuelan equine encephalitis virus is strain TC-83.

21. The composition of claim 18, wherein the RNA polymerase complex region comprises sequence encoding for nsP1-4.

22. The composition of claim 1, wherein the composition is formulated as a dry powder.

* * * * *